US007288689B2

(12) United States Patent
Janssen et al.

(10) Patent No.: US 7,288,689 B2
(45) Date of Patent: Oct. 30, 2007

(54) METHANOL AND FUEL ALCOHOL PRODUCTION FOR AN OXYGENATE TO OLEFIN REACTION SYSTEM

(75) Inventors: Marcel Johannes Janssen, Kessel-Lo (BE); Cornelis F. Van Egmond, Pasadena, TX (US); Luc R. M. Martens, Meise (BE); Jaimes Sher, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 296 days.

(21) Appl. No.: 10/716,685

(22) Filed: Nov. 19, 2003

(65) Prior Publication Data

US 2005/0107481 A1 May 19, 2005

(51) Int. Cl.
*C07C 1/00* (2006.01)
*C07C 27/00* (2006.01)

(52) U.S. Cl. ............. 585/640; 585/639; 518/700; 518/703; 518/707; 518/713; 518/714

(58) Field of Classification Search ........ 585/638–640; 518/700, 703, 707, 713, 714
See application file for complete search history.

(56) References Cited

U.S. PATENT DOCUMENTS

| 4,014,913 | A | 3/1977 | Ellgen et al. ............... 260/449 |
| 4,111,837 | A | 9/1978 | Taylor ........................ 252/430 |
| 4,122,110 | A | 10/1978 | Sugier et al. ............ 260/449.5 |
| 4,133,966 | A | 1/1979 | Pretzer et al. .............. 568/902 |
| 4,233,466 | A | 11/1980 | Fiato ......................... 568/902 |
| 4,239,924 | A | 12/1980 | Pretzer et al. ............. 568/902 |
| 4,239,925 | A | 12/1980 | Pretzer et al. ............. 568/902 |
| 4,253,987 | A | 3/1981 | Fiato .................... 252/429 R |
| 4,270,015 | A | 5/1981 | Knifton ...................... 585/324 |
| 4,304,946 | A | 12/1981 | Isogai et al. ................ 568/902 |
| 4,324,927 | A | 4/1982 | Gauthier-Lafaye et al. . 568/902 |
| 4,328,379 | A | 5/1982 | Devon ........................ 568/902 |
| 4,339,545 | A | 7/1982 | Knifton ...................... 518/700 |
| 4,371,724 | A | 2/1983 | Lin et al. .................... 568/902 |
| 4,398,050 | A | 8/1983 | Hofstadt et al. ............ 585/640 |
| 4,424,383 | A | 1/1984 | Cornils et al. ............. 568/902 |
| 4,424,384 | A | 1/1984 | Lin et al. .................... 568/902 |
| 4,596,782 | A | 6/1986 | Courty et al. ............... 502/302 |
| 4,605,677 | A | 8/1986 | Knifton ...................... 518/700 |
| 4,622,343 | A | 11/1986 | Knifton et al. ............. 518/700 |
| 4,638,106 | A | 1/1987 | Pieters et al. .............. 585/640 |
| 4,670,620 | A | 6/1987 | Jacobs et al. ............... 585/640 |
| 4,698,452 | A | 10/1987 | Le Van Mao et al. ...... 585/640 |
| 4,751,248 | A | 6/1988 | Lin et al. .................... 518/707 |
| 4,752,623 | A | 6/1988 | Stevens et al. ............. 518/714 |
| 4,791,141 | A | 12/1988 | Chaumette et al. ......... 518/713 |
| 4,822,825 | A | * | 4/1989 | Bhattacharya et al. ...... 518/714 |
| 4,825,013 | A | 4/1989 | Quarderer et al. ....... 568/902.2 |
| 4,954,665 | A | 9/1990 | Vidal ..................... 568/902.2 |
| 5,070,016 | A | 12/1991 | Hallberg ..................... 435/132 |
| 5,169,869 | A | 12/1992 | Miller et al. ................ 518/713 |
| 5,493,064 | A | 2/1996 | Vanderspurt et al. ....... 568/905 |
| 5,627,295 | A | 5/1997 | Sofianos et al. ............. 556/27 |
| 5,756,421 | A | 5/1998 | Choudhary et al. ......... 502/328 |
| 6,114,279 | A | * | 9/2000 | Fukui et al. ................ 502/342 |
| 6,441,262 | B1 | 8/2002 | Fung et al. ................. 585/640 |
| 2001/0047040 | A1 | 11/2001 | Agee et al. ................. 518/704 |

FOREIGN PATENT DOCUMENTS

| DE | 31 13 838 | 1/1982 |
| DE | 257 740 | 6/1988 |
| EP | 109 645 | 5/1984 |
| GB | 2 078 745 | 1/1982 |
| GB | 2 083 465 | 3/1982 |
| WO | 2004/060841 | 7/2004 |

OTHER PUBLICATIONS

DialogIP Abstract for DD 257740, Jun. 29, 1988.
DialogIP Abstract for DE 31 13 838, Jan. 7, 1982.
Thomson Derwent Abstract for EP 109 645, May 30, 1984 entitled "Simultaneous Production of Methanol and Ethanol".
J P Leonard et al: "Non-Conventional Sources for Ethylene?" Energy Progress, vol. 1, No. 1-4, 1981, pp. 41-44, US New York, NY.
Database Chemabs 'Online! Chemical Abstracts Service, Columbus, Ohio, US; Takeuchi, Kazuhiko: "Synthetic process of basic chemicals from syngas", retrieved from STN Database accession No. 1997: 2165 *abstract* & Shokubai, 38(8), 604-610 Coden: Shkuaj; ISSN: 0559-8958, 1996.
U.S. Appl. No. 10/717,006, filed Nov. 19, 2003, "Controlling The Ratio Of Ethylene To Propylene Produced In A Methanol/Ethanol Conversion Process", Inventors: Jaimes Sher, Cor F. van Egmond, Luc R.M. Martens, Marcel Janssen, James Lattner, and Teng Xu.
U.S. Appl. No. 10/716,894, filed Nov. 19, 2003, "Methanol And Ethanol Production For An Oxygenate To Olefin Reaction System", Inventors: Cor F. van Egmond, Andrew Argo, Teng Xu, Marcel Janssen, and Jamies Sher.
Japanese Journal article Kazuhiko Takeuchi, "Synthetic Process of Basic Chemicals from Syngas," 38(8) Shokubai Gakkai pp. 604-610 (1996). (Abstract).
Yamamoto and Inui, "Highly Effective Synthesis of Ethanol from $CO_2$ on Fe, Cu-Based Novel Catalysts", *Advances in Chemical Conversions for Mitigating Carbon Dioxide*, Studies in Surface Science and Catalysis, vol. 114, 1998 Elsevier Science B.V., pp. 513-516.
Scheeline, et al, "Ethylene By Methanol Homologation", Process Economics Program, SRI International, Menio Park, California, PEP Review No. 80-1-3, (Mar. 1981), pp. 1-20.
"Alternative Fuels and Chemicals From Synthesis Gas", Technical Progress Report No. 37, For the Period Jan. 1-Mar. 31, 1999, Air Products and Chemicals, Inc., Prepared for the United States Department of Energy, pp. 1-26.
Norcio, et al, "Higher Alcohol Synthesis From Methanol or Syngas", Department of Chemical Engineering, pp. 37-41, date not available.

* cited by examiner

*Primary Examiner*—Glenn Caldarola
*Assistant Examiner*—In Suk Bullock
(74) *Attorney, Agent, or Firm*—David M. Weisberg

(57) ABSTRACT

The present invention provides various processes for producing C1 to C4 alcohols, optionally in a mixed alcohol stream, and optionally converting the alcohols to light olefins. In one embodiment, the invention includes directing a first portion of a syngas stream to a methanol synthesis zone wherein methanol is synthesized. A second portion of the syngas stream is directed to a fuel alcohol synthesis zone wherein fuel alcohol is synthesized. The methanol and at least a portion of the fuel alcohol are directed to an oxygenate to olefin reaction system for conversion thereof to ethylene and propylene.

47 Claims, 3 Drawing Sheets

METHANOL AND FUEL ALCOHOL PRODUCTION FOR AN OXYGENATE TO OLEFIN REACTION SYSTEM

FIELD OF THE INVENTION

The present invention relates to processes for forming light olefins. More particularly, the present invention relates to processes for forming light olefins from a mixed alcohol feedstock comprising methanol and fuel alcohol.

BACKGROUND OF THE INVENTION

Light olefins, defined herein as ethylene and propylene, are important commodity petrochemicals useful in a variety of processes for making plastics and other chemical compounds. Ethylene is used to make various polyethylene plastics, and in making other chemicals vinyl chloride, ethylene oxide, ethyl benzene and alcohol. Propylene is used to make various polypropylene plastics, and in making other chemicals such as acrylonitrile and propylene oxide.

The petrochemical industry has known for some time that oxygenates, especially alcohols, are convertible into light olefins. The preferred conversion process is generally referred to as an oxygenate to olefin (OTO) reaction process. Specifically, in an OTO reaction process, an oxygenate contacts a molecular sieve catalyst composition under conditions effective to convert at least a portion of the oxygenate to light olefins. When methanol is the oxygenate, the process is generally referred to as a methanol to olefin (MTO) reaction process. Methanol is a particularly preferred oxygenate for the synthesis of ethylene and/or propylene.

Depending on the respective commercial markets for ethylene and propylene, it may be desirable to vary the weight ratio of ethylene to propylene formed in an OTO reaction system. It has recently been discovered, however, that although percent conversion may vary with a change in reaction conditions, e.g., temperature or pressure, the selectivity of a methanol-containing feedstock for ethylene and propylene in an OTO reaction system generally remains constant with changes in reaction conditions. Thus, the need exists in the art for a process for varying the ratio of ethylene to propylene formed in an OTO reaction system.

SUMMARY OF THE INVENTION

This invention provides processes for forming ethylene and propylene from an alcohol-containing feedstock comprising methanol and fuel alcohol. As used herein, "fuel alcohol" means an alcohol-containing composition comprising ethanol, one or more C3 alcohols, one or more C4 alcohols and optionally one or more C5+ alcohols. Optionally, the methanol in the alcohol-containing feedstock is formed in a process for converting syngas to methanol in the presence of a methanol synthesis catalyst composition, while the fuel alcohol in the alcohol-containing feedstock is formed from a reaction of syngas over a fuel alcohol synthesis catalyst. The alcohol-containing feedstock is directed to an oxygenate to olefin (OTO) reaction system for the conversion thereof to ethylene and propylene. The resulting weight ratio of ethylene to propylene formed in the OTO reaction system advantageously can be varied by varying the weight ratio of the methanol to fuel alcohols in the alcohol-containing feedstock that is directed to the OTO reaction system.

In one embodiment, the invention is to a process for forming light olefins from an alcohol-containing stream. In this embodiment, the invention includes a step of providing an alcohol-containing stream comprising methanol, ethanol a C3 alcohol and a C4 alcohol. At least a portion of the alcohol-containing stream contacts a molecular sieve catalyst composition in a reaction zone under conditions effective to form ethylene and propylene. The alcohol-containing stream optionally comprises less than about 90 weight percent methanol, less than about 85 weight percent methanol, or less than about 80 weight percent methanol, based on the total weight of the alcohol-containing stream. Additionally or alternatively, the alcohol-containing stream has a methanol to C2-C4 alcohol weight ratio of from about 0.1 to about 4.0, preferably from about 0.33 to about 3.0.

By varying the ratio of the methanol to C2-C4 alcohols in the alcohol-containing stream, the ratio of the ethylene to propylene formed advantageously can be controlled. In one embodiment, the ethylene and propylene are yielded in an effluent stream having an ethylene to propylene weight ratio of greater than 1.0, preferably from about 1.1 to about 2.5, and most preferably from about 1.2 to about 2.0. The ethylene and propylene thus formed optionally are polymerized. Thus, the process optionally further includes a step of separating a majority of the ethylene from a majority of the propylene to form an ethylene-containing stream and a propylene-containing stream. The ethylene-containing stream optionally is contacted with a polymerization catalyst under conditions effective to convert at least a portion of the ethylene contained therein to polyethylene. Additionally or alternatively, the propylene-containing stream is contacted with a polymerization catalyst under conditions effective to convert at least a portion of the propylene contained therein to polypropylene.

Preferably, the molecular sieve catalyst composition comprises a small pore zeolite or a molecular sieve selected from the group consisting of: MeAPSO, SAPO-5, SAPO-8, SAPO-11, SAPO-16, SAPO-17, SAPO-18, SAPO-20, SAPO-031, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

Optionally, the process also includes steps of providing a methanol-containing stream comprising the methanol, and providing a fuel alcohol-containing stream comprising the ethanol, the C3 alcohol and the C4 alcohol. In this embodiment, the methanol-containing stream and the fuel alcohol-containing stream are combined to form the alcohol-containing stream. The fuel alcohol-containing stream optionally comprises less than about 60 weight percent methanol, less than about 65 weight percent methanol, or less than about 75 weight percent methanol, based on the total weight of the fuel alcohol-containing stream. Additionally or alternatively, the fuel alcohol-containing stream comprises at least about 10 weight percent ethanol or at least about 25 weight percent ethanol, based on the total weight of the fuel alcohol-containing stream. Additionally or alternatively, the fuel alcohol-containing stream comprises at least about 10 weight percent C3-C4 alcohols, based on the total weight of the fuel alcohol-containing stream.

Preferably, the fuel alcohol-containing stream is formed by contacting syngas with a fuel alcohol synthesis catalyst comprising a microporous zeolitic material under conditions effective to convert the syngas to the fuel alcohol-containing stream. Optionally, the fuel alcohol synthesis catalyst comprises one or more of $Cu/ZnO/Cr_2O_3$ and $Cu/ZnO/Al_2O_3$, optionally alkali promoted. Additionally or alternatively, the fuel alcohol synthesis catalyst comprises an oxide of one or more of zinc, chromium, copper, cobalt, and nickel, and the fuel alcohol synthesis catalyst optionally is alkali, lanthanum or cerium promoted. Additionally or alternatively, the fuel alcohol synthesis catalyst comprises one or more of $MoS_2$ and $Co/MoS_2$, and the fuel alcohol synthesis catalyst optionally is alkali promoted.

Optionally, the methanol in the methanol-containing stream is formed by contacting syngas with a methanol synthesis catalyst under conditions effective to convert the syngas to the methanol in the methanol-containing stream. The methanol synthesis catalyst preferably comprises an oxide of one or more of copper, zinc and aluminum.

In another embodiment, the invention includes a step of contacting a first syngas stream comprising carbon monoxide, carbon dioxide and hydrogen with a methanol synthesis catalyst under first conditions effective to form a methanol-containing stream comprising methanol and water. A second syngas stream comprising carbon monoxide, carbon dioxide and hydrogen contacts a fuel alcohol synthesis catalyst under second conditions effective to form a fuel alcohol-containing stream comprising ethanol, propanol and butanol. These two contacting steps preferably occur in parallel to one another. At least a portion of the methanol-containing stream is combined with at least a portion of the fuel alcohol-containing stream to form a combined stream, which contacts a molecular sieve catalyst composition in a reaction zone under third conditions effective to form ethylene and propylene. Optionally, the process further includes a step of removing water from the combined stream before the at least a portion of the methanol-containing stream contacts the molecular sieve catalyst composition.

The syngas optionally is derived from natural gas. In this embodiment, the invention optionally includes a step of contacting a natural gas stream with oxygen under fourth conditions effective to convert the natural gas stream into an initial syngas stream, which optionally is separated into the first syngas stream and the second syngas stream.

In another embodiment, the invention is to a process for producing an alcohol mixture suitable for use as a feedstock for an oxygenate to olefin reaction system. In this embodiment, the invention includes a step of contacting a first syngas stream comprising carbon monoxide, carbon dioxide and hydrogen with a methanol synthesis catalyst under first conditions effective to form a methanol-containing stream comprising methanol and water. A second syngas stream comprising carbon monoxide, carbon dioxide and hydrogen contacts a fuel alcohol synthesis catalyst under second conditions effective to form a fuel alcohol-containing stream comprising ethanol, propanol and butanol. These two contacting steps preferably occur in parallel to one another. At least a portion of the methanol-containing stream is combined with at least a portion of the fuel alcohol-containing stream to form a combined stream, which has a methanol to C2-C4 alcohol weight ratio of from about 0.1 to about 4.0, preferably from about 0.33 to about 3.0, and most preferably from about 0.5 to about 1.0. This process optionally includes a step of directing the combined stream or a portion thereof, optionally an aliquot portion of the combined stream or a non-aliquot portion of the combined stream, to an oxygenate to olefin reaction system. Water optionally is removed from the combined stream to form a dry combined stream, which optionally comprises less than about 10 weight percent water, based on the total weight of the dry combined stream.

In another embodiment, the invention is directed to a process for producing light olefins. This process includes a step of contacting a first syngas stream comprising carbon monoxide, carbon dioxide and hydrogen with a methanol synthesis catalyst under first conditions effective to form a methanol-containing stream comprising methanol and water. A second syngas stream comprising carbon monoxide, carbon dioxide and hydrogen contacts a fuel alcohol synthesis catalyst under second conditions effective to form a fuel alcohol-containing stream comprising ethanol, propanol and butanol. These two contacting steps preferably occur in parallel to one another. At least a portion of the methanol-containing stream is combined with at least a portion of the fuel alcohol-containing stream to form a combined stream, at least a portion of which contacts a molecular sieve catalyst composition in a reaction system under third conditions effective to convert the methanol, the ethanol, optionally the propanol and optionally the butanol to light olefins. An effluent stream is yielded from the reaction system. The effluent stream comprises ethylene and propylene and has an ethylene to propylene weight ratio of from about 0.9 to about 3.0, preferably from about 1.1 to about 2.5, and most preferably from about 1.2 to about 1.5.

BRIEF DESCRIPTION OF THE DRAWINGS

This invention will be better understood by reference to the detailed description of the invention when taken together with the attached drawings, wherein.

DETAILED DESCRIPTION OF THE INVENTION

A. Introduction

Figure 1:
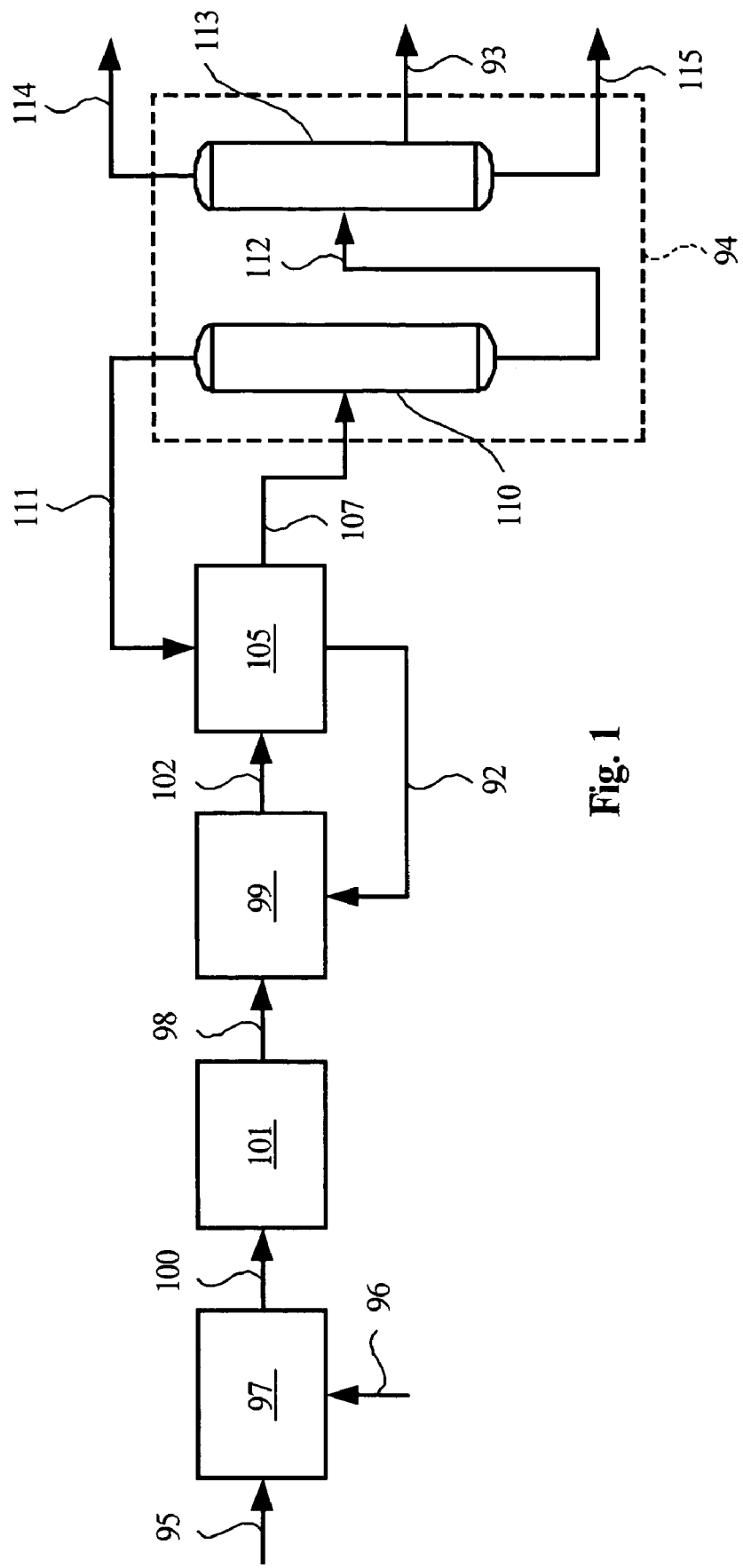
FIG. 1 is a flow diagram of a methanol synthesis system.

The present invention provides processes for forming an alcohol-containing stream comprising both methanol and fuel alcohol. As used herein, "fuel alcohol" means an alcohol-containing composition comprising ethanol, one or more C3 alcohols and one or more C4 alcohols. The methanol in the alcohol-containing stream is formed in a process for converting syngas to methanol in the presence of a catalyst composition. The fuel alcohol in the alcohol-containing stream is formed from a fuel alcohol synthesis reaction or reactions of syngas in the presence of a fuel alcohol synthesis catalyst. The alcohol-containing stream preferably is directed to an oxygenate to olefin (OTO) reaction system, wherein the methanol and fuel alcohol contained in the alcohol-containing stream are converted to ethylene and propylene, optionally one or more butenes and/or optionally one or more pentenes.

According to one preferred embodiment of the present invention, the resulting weight ratio of ethylene to propylene that is formed in the OTO reaction system can be varied by varying the weight ratio of the methanol to fuel alcohol contained in the alcohol-containing stream that is directed to the OTO reaction system. Thus, in one embodiment, the present invention is directed to an integrated system wherein methanol is synthesized in a methanol synthesis unit, and fuel alcohol is synthesized in a fuel alcohol synthesis unit. Preferably the methanol and the fuel alcohol are combined to form a combined stream, which is directed to an OTO reaction system for the formation of ethylene and propylene. A detailed description of methanol synthesis systems will now be described.

B. Methanol Synthesis Systems

1. EXAMPLES OF METHANOL SYNTHESIS PROCESS

There are numerous technologies available for producing methanol including fermentation or the reaction of synthesis gas (syngas) derived from a hydrocarbon feed stream, which may include natural gas, petroleum liquids, carbonaceous materials including coal, recycled plastics, municipal waste or any other organic material. Methanol is typically synthesized from the catalytic reaction of syngas in a methanol synthesis reactor in the presence of a heterogeneous catalyst. For example, in one synthesis process methanol is produced using a copper/zinc oxide catalyst in a water-cooled tubular methanol reactor. Syngas is defined as a gas comprising carbon monoxide (CO), hydrogen ($H_2$) and optionally carbon dioxide ($CO_2$). Optionally, syngas may also include unreacted feedstocks such as methane ($CH_4$), ethane, propane, heavier hydrocarbons, or other compounds. Generally, the production of syngas involves a reforming reaction of natural gas, mostly methane, and an oxygen source into hydrogen, carbon monoxide and/or carbon dioxide. Syngas production processes are well known, and include conventional steam reforming, autothermal reforming, or a combination thereof.

Methanol compositions can be manufactured from a hydrocarbon feed stream derived from a variety of carbon sources. Examples of such sources include biomass, natural gas, C1-C5 hydrocarbons, naphtha, heavy petroleum oils, or coke (i.e., coal). Preferably, the hydrocarbon feed stream comprises methane in an amount of at least about 50% by volume, more preferably at least about 70% by volume, most preferably at least about 80% by volume. In one embodiment of this invention natural gas is the preferred hydrocarbon feed source.

One way of converting the carbon source to a methanol composition is to first convert the carbon source to syngas, and then convert the syngas to the methanol composition. Any conventional process can be used. In particular, any conventional carbon oxide conversion catalyst can be used to convert the syngas to the methanol composition. In one embodiment, the carbon oxide conversion catalyst is a nickel containing catalyst.

The hydrocarbon feed stream that is used in the conversion of hydrocarbon to syngas is optionally treated to remove impurities that can cause problems in further processing of the hydrocarbon feed stream. These impurities can poison many conventional propylene and ethylene forming catalysts. A majority of the impurities that may be present can be removed in any conventional manner. The hydrocarbon feed is preferably purified to remove sulfur compounds, nitrogen compounds, particulate matter, other condensables, and/or other potential catalyst poisons prior to being converted into syngas.

In one embodiment of the invention, the hydrocarbon feed stream is passed to a syngas plant. The syngas preferably has an appropriate molar ratio of hydrogen to carbon oxide (carbon monoxide and/or carbon dioxide), as described below. The syngas plant may employ any conventional means of producing syngas, including partial oxidation, steam or $CO_2$ reforming, or a combination of these two chemistries.

Steam reforming generally comprises contacting a hydrocarbon with steam to form syngas. The process preferably includes the use of a catalyst.

Partial oxidation generally comprises contacting a hydrocarbon with oxygen or an oxygen-containing gas such as air to form syngas. Partial oxidation takes place with or without the use of a catalyst, although the use of a catalyst is preferred. In one embodiment, water (steam) is added with the feed in the partial oxidation process. Such an embodiment is generally referred to as autothermal reforming.

Conventional syngas-generating processes include gas phase partial oxidation, autothermal reforming, fluid bed syngas generation, catalytic partial oxidation and various processes for steam reforming.

2. Steam Reforming to Make Syngas

In the catalytic steam reforming process, hydrocarbon feeds are converted to a mixture of $H_2$, CO and $CO_2$ by reacting hydrocarbons with steam over a catalyst. This process involves the following reactions:

$$CH_4 + H_2O \rightarrow CO + 3H_2 \tag{1}$$

or $$C_nH_m + nH_2O \rightarrow nCO + [n+(m/2)]H_2 \text{ and} \tag{2}$$

$$CO + H_2O \rightarrow CO_2 + H_2 \text{ (shift reaction)} \tag{3}$$

The reaction is carried out in the presence of a catalyst. Any conventional reforming type catalyst can be used. The catalyst used in the step of catalytic steam reforming comprises at least one active metal or metal oxide of Group 6 or Group 8-10 of the Periodic Table of the Elements. The Periodic Table of the Elements referred to herein is that from CRC Handbook of Chemistry and Physics, 82nd Edition, 2001-2002, CRC Press LLC, which is incorporated herein by reference.

In one embodiment, the catalyst contains at least one Group 6 or Group 8-10 metal, or oxide thereof, having an atomic number of 28 or greater. Specific examples of reforming catalysts that can be used are nickel, nickel oxide, cobalt oxide, chromia and molybdenum oxide. Optionally, the catalyst is employed with at least one promoter. Examples of promoters include alkali and rare earth promoters. Generally, promoted nickel oxide catalysts are preferred.

The amount of Group 6 or Group 8-10 metals in the catalyst can vary. Preferably, the catalyst includes from about 3 wt % to about 40 wt % of at least one Group 6 or Group 8-10 metal, based on total weight of the catalyst. Preferably, the catalyst includes from about 5 wt % to about 25 wt % of at least one Group 6 or Group 8-10 metal, based on total weight of the catalyst.

The reforming catalyst optionally contains one or more metals to suppress carbon deposition during steam reforming. Such metals are selected from the metals of Group 14 and Group 15 of the Periodic Table of the Elements. Preferred Group 14 and Group 15 metals include germanium, tin, lead, arsenic, antimony, and bismuth. Such metals are preferably included in the catalyst in an amount of from about 0.1 wt % to about 30 wt %, based on total weight of nickel in the catalyst.

In a catalyst comprising nickel and/or cobalt there may also be present one or more platinum group metals, which are capable of increasing the activity of the nickel and/or cobalt and of decreasing the tendency to carbon lay-down when reacting steam with hydrocarbons higher than methane. The concentration of such platinum group metal is typically in the range 0.0005 to 0.1 wt. % as metal, calculated as the whole catalyst unit. Further, the catalyst, especially in preferred forms, can contain a platinum group metal but no non-noble catalytic component. Such a catalyst is more suitable for the hydrocarbon steam reforming reaction than one containing a platinum group metal on a conventional support because a greater fraction of the active metal is accessible to the reacting gas. A typical content of platinum group metal when used alone is in the range 0.0005 to 0.5% w/w as metal, calculated on the whole catalytic unit.

In one embodiment, the reformer unit includes tubes which are packed with solid catalyst granules. Preferably, the solid catalyst granules comprise nickel or other catalytic agents deposited on a suitable inert carrier material. More preferably, the catalyst is NiO supported on calcium aluminate, alumina, spinel type magnesium aluminum oxide or calcium aluminate titanate.

In yet another embodiment, both the hydrocarbon feed stream and the steam are preheated prior to entering the reformer. The hydrocarbon feedstock is preheated up to as high a temperature as is consistent with the avoiding of undesired pyrolysis or other heat deterioration. Since steam reforming is endothermic in nature, and since there are practical limits to the amount of heat that can be added by indirect heating in the reforming zones, preheating of the feed is desired to facilitate the attainment and maintenance of a suitable temperature within the reformer itself. Accordingly, it is desirable to preheat both the hydrocarbon feed and the steam to a temperature of at least 200° C.; preferably at least 400° C. The reforming reaction is generally carried out at a reformer temperature of from about 500° C. to about 1,200° C., preferably from about 800° C. to about 1,100° C., and more preferably from about 900° C. to about 1,050° C.

Gas hourly space velocity in the reformer should be sufficient for providing the desired CO to $CO_2$ balance in the syngas. Preferably, the gas hourly space velocity (based on wet feed) is from about 3,000 per hour to about 10,000 per hour, more preferably from about 4,000 per hour to about 9,000 per hour, and most preferably from about 5,000 per hour to about 8,000 per hour.

Any conventional reformer can be used in the step of catalytic steam reforming. The use of a tubular reformer is preferred. Preferably, the hydrocarbon feed is passed to a tubular reformer together with steam, and the hydrocarbon and steam contact a steam reforming catalyst. In one embodiment, the steam reforming catalyst is disposed in a plurality of furnace tubes that are maintained at an elevated temperature by radiant heat transfer and/or by contact with combustion gases. Fuel, such as a portion of the hydrocarbon feed, is burned in the reformer furnace to externally heat the reformer tubes therein. See, for example, Kirk-Othmer, Encyclopedia of Chemical Technology, 3rd Ed., 1990, vol. 12, p. 951; and Ullmann's Encyclopedia of Industrial Chemistry, 5th Ed., 1989, vol. A-12, p. 186, the relevant portions of each being fully incorporated herein by reference.

The ratio of steam to hydrocarbon feed will vary depending on the overall conditions in the reformer. The amount of steam employed is influenced by the requirement of avoiding carbon deposition on the catalyst, and by the acceptable methane content of the effluent at the reforming conditions maintained. On this basis, the mole ratio of steam to hydrocarbon feed in the conventional primary reformer unit is preferably from about 1.5:1 to about 5:1, preferably from about 2:1 to about 4:1.

Typically, the syngas formed comprises hydrogen and a carbon oxide. The hydrogen to carbon oxide ratio of the syngas produced will vary depending on the overall conditions of the reformer. Preferably, the molar ratio of hydrogen to carbon oxide in the syngas will range from about 1:1 to about 5:1. More preferably the molar ratio of hydrogen to carbon oxide will range from about 2:1 to about 3:1. Even more preferably the molar ratio of hydrogen to carbon oxide will range from about 2:1 to about 2.5:1. Most preferably the molar ration of hydrogen to carbon oxide will range from about 2:1 to about 2.3:1.

Steam reforming is generally carried out at superatmospheric pressure. The specific operating pressure employed is influenced by the pressure requirements of the subsequent process in which the reformed gas mixture is to be employed. Although any superatmospheric pressure can be used in practicing the invention, pressures of from about 175 psig (1,308 kPa abs.) to about 1,100 psig (7,686 kPa abs.) are desirable. Preferably, steam reforming is carried out at a pressure of from about 300 psig (2,170 kPa abs.) to about 800 psig (5,687 kPa abs.), more preferably from about 350 psig (2,515 kPa abs.) to about 700 psig (4,928 kPa abs.).

3. Partial Oxidation to Make Syngas

The invention optionally provides for the production of syngas, or CO and $H_2$, by oxidative conversion (also referred to herein as partial oxidation) of hydrocarbons, particularly natural gas and $C_1$-$C_5$ hydrocarbons. According to the process, one or more hydrocarbons are reacted with free-oxygen to form CO and $H_2$. The process is carried out with or without a catalyst. The use of a catalyst is preferred, preferably with the catalyst containing at least one non-transition or transition metal oxides. The process is essentially exothermic, and is an incomplete combustion reaction, having the following general formula:

$$C_nH_m + (n/2)O_2 \to nCO + (m/2)H_2 \qquad (4)$$

Non-catalytic partial oxidation of hydrocarbons to $H_2$, CO and $CO_2$ is desirably used for producing syngas from heavy fuel oils, primarily in locations where natural gas or lighter hydrocarbons, including naphtha, are unavailable or uneconomical compared to the use of fuel oil or crude oil. The non-catalytic partial oxidation process is carried out by injecting preheated hydrocarbon, oxygen and steam through a burner into a closed combustion chamber. Preferably, the individual components are introduced at a burner where they meet in a diffusion flame, producing oxidation products and heat. In the combustion chamber, partial oxidation of the hydrocarbons generally occurs with less than stoichiometric oxygen at very high temperatures and pressures. Preferably, the components are preheated and pressurized to reduce reaction time. The process preferably occurs at a temperature of from about 1,350° C. to about 1,600° C., and at a pressure of from above atmospheric to about 150 atm.

Catalytic partial oxidation comprises passing a gaseous hydrocarbon mixture, and oxygen, preferably in the form of air, over reduced or unreduced composite catalysts. The reaction is optionally accompanied by the addition of water vapor (steam). When steam is added, the reaction is generally referred to as autothermal reduction. Autothermal reduction is both exothermic and endothermic as a result of adding both oxygen and water.

In the partial oxidation process, the catalyst comprises at least one transition element selected from the group consisting of Ni, Co, Pd, Ru, Rh, Ir, Pt, Os and Fe. Preferably, the catalyst comprises at least one transition element selected from the group consisting of Pd, Pt, and Rh. In another embodiment, preferably the catalyst comprises at least one transition element selected form the group consisting of Ru, Rh, and Ir.

In one embodiment, the partial oxidation catalyst further comprises at least one metal selected from the group consisting of Ti, Zr, Hf, Y, Th, U, Zn, Cd, B, Al, Tl, Si, Sn, Pb, P, Sb, Bi, Mg, Ca, Sr, Ba, Ga, V, and Sc. Also, optionally included in the partial oxidation catalyst is at least one rare earth element selected from the group consisting of La, Ce, Pr, Nd, Pm, Sm, Eu, Gd, Tb, Dy, Ho, Er, Tm, Yb and Lu.

In another embodiment the catalyst employed in the process may comprise a wide range of catalytically active components, for example Pd, Pt, Rh, Ir, Os, Ru, Ni, Cr, Co, Ce, La and mixtures thereof. Materials not normally considered to be catalytically active may also be employed as catalysts, for example refractory oxides such as cordierite, mullite, mullite aluminum titanate, zirconia spinels and alumina.

In yet another embodiment, the catalyst is comprised of metals selected from those having atomic number 21 to 29, 40 to 47 and 72 to 79, the metals Sc, Ti V, Cr, Mn, Fe, Co, Ni, Cu, Zr, Nb, Mo, Tc, Ru, Rh, Pd, Ag, Hf, Ta, W, Re, Os Ir, Pt, and Au. The preferred metals are those in Group 8 of the Periodic Table of the Elements, that is Fe, Os, Co, Re, Ir, Pd, Pt, Ni, and Ru.

In another embodiment, the partial oxidation catalyst comprises at least one transition or non-transition metal deposited on a monolith support. The monolith supports are preferably impregnated with a noble metal such as Pt, Pd or Rh, or other transition metals such as Ni, Co, Cr and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

In one embodiment, the catalyst is retained in form of a fixed arrangement. The fixed arrangement generally comprises a fixed bed of catalyst particles. Alternatively, the fixed arrangement comprises the catalyst in the form of a monolith structure. The fixed arrangement may consist of a single monolith structure or, alternatively, may comprise a number of separate monolith structures combined to form the fixed arrangement. A preferred monolith structure comprises a ceramic foam. Suitable ceramic foams for use in the process are available commercially.

In yet another embodiment, the feed comprises methane, and the feed is injected with oxygen into the partial oxidation reformer at a methane to oxygen (i.e., $O_2$) ratio of from about 1.2:1 to about 10:1. Preferably the feed and oxygen are injected into the reformer at a methane to oxygen ratio of from about 1.6:1 to about 8:1, more preferably from about 1.8:1 to about 4:1.

Water may or may not be added to the partial oxidation process. When added, the concentration of water injected into the reformer is not generally greater than about 65 mole %, based on total hydrocarbon and water feed content. Preferably, when water is added, it is added at a water to methane ratio of not greater than 3:1, preferably not greater than 2:1.

The catalyst may or may not be reduced before the catalytic reaction. In one embodiment, the catalyst is reduced and reduction is carried out by passing a gaseous mixture comprising hydrogen and inert gas (e.g., $N_2$, He, or Ar) over the catalyst in a fixed bed reactor at a catalyst reduction pressure of from about 1 atm to about 5 atm, and a catalyst reduction temperature of from about 300° C. to about 700° C. Hydrogen gas is used as a reduction gas, preferably at a concentration of from about 1 mole % to about 100 mole %, based on total amount of reduction gas. Desirably, the reduction is further carried out at a space velocity of reducing gas mixture of from about 103 $cm^3/g \cdot hr$ to about 105 $cm^3/g$ hr for a period of from about 0.5 hour to about 20 hours.

In one embodiment, the partial oxidation catalyst is not reduced by hydrogen. When the catalyst is not reduced by hydrogen before the catalytic reaction, the reduction of the catalyst can be effected by passing the hydrocarbon feed and oxygen (or air) over the catalyst at temperature in the range of from about 500° C. to about 900° C. for a period of from about 0.1 hour to about 10 hours.

In the partial oxidation process, carbon monoxide (CO) and hydrogen ($H_2$) are formed as major products, and water and carbon dioxide ($CO_2$) as minor products. The gaseous product stream comprises the above mentioned products, unconverted reactants (i.e. methane or natural gas and oxygen) and components of feed other than reactants.

When water is added in the feed, the $H_2$:CO mole ratio in the product is increased by the shift reaction: $CO+H_2O$ $H_2+CO_2$. This reaction occurs simultaneously with the oxidative conversion of the hydrocarbon in the feed to CO and H2 or syngas. The hydrocarbon used as feed in the partial oxidation process is, preferably in the gaseous phase when contacting the catalyst. The partial oxidation process is particularly suitable for the partial oxidation of methane, natural gas, associated gas or other sources of light hydrocarbons. In this respect, the term "light hydrocarbons" is a reference to hydrocarbons having from 1 to 5 carbon atoms. The process may be advantageously applied in the conversion of gas from naturally occurring reserves of methane which contain substantial amounts of carbon dioxide. In one embodiment, the hydrocarbon feed preferably contains from about 10 mole % to about 90 mole % methane, based on total feed content. More preferably, the hydrocarbon feed contains from about 20 mole % to about 80 mole % methane, based on total feed content. In another embodiment, the feed comprises methane in an amount of at least 50% by volume, more preferably at least 70% by volume, and most preferably at least 80% by volume.

In one embodiment of the invention, the hydrocarbon feedstock is contacted with the catalyst in a mixture with an oxygen-containing gas. Air is suitable for use as the oxygen-containing gas. Substantially pure oxygen as the oxygen-containing gas is preferred on occasions where there is a need to avoid handling large amounts of inert gas such as nitrogen. The feed optionally comprises steam.

In another embodiment of the invention, the hydrocarbon feedstock and the oxygen-containing gas are preferably present in the feed in such amounts as to give an oxygen-to-carbon ratio in the range of from about 0.3:1 to about 0.8:1, more preferably, in the range of from about 0.45:1 to about 0.75:1. References herein to the oxygen-to-carbon ratio refer to the ratio of oxygen in the from of oxygen molecules ($O_2$) to carbon atoms present in the hydrocarbon feedstock. Preferably, the oxygen-to-carbon ratio is in the range of from about 0.45:1 to about 0.65:1, with oxygen-to-carbon ratios in the region of the stoichiometric ratio of 0.5: 1, that is ratios in the range of from about 0.45:1 to about 0.65:1, being more preferred. When steam is present in the feed, the steam-to-carbon ratio is not greater than about 3.0:1, more preferably not greater than about 2.0:1. The hydrocarbon feedstock, the oxygen-containing gas and steam, if present, are preferably well mixed prior to being contacted with the catalyst.

The partial oxidation process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 150 bars. Preferably, the partial oxidation process is operated at a pressure in the range of from about 2 bars to about 125 bars, more preferably from about 5 bars to about 100 bars.

The partial oxidation process is also operable over a wide range of temperatures. At commercial scale, the feed is preferably contacted with the catalyst at high temperatures. In one embodiment, the feed mixture is contacted with the catalyst at a temperature in excess of 600° C. Preferably, the feed mixture is contacted with the catalyst at a temperature in the range of from about 600° C. to about 1,700° C., more preferably from about 800° C. to about 1,600° C. The feed mixture is preferably preheated prior to contacting the catalyst.

The feed is provided during the operation of the process at a suitable space velocity to form a substantial amount of CO in the product. In one embodiment, gas space velocities (expressed in normal liters of gas per kilogram of catalyst per hour) are in the range of from about 20,000 Nl/kg/hr to about 100,000,000 Nl/kg/hr, more preferably in the range of from about 50,000 Nl/kg/hr to about 50,000,000 Nl/kg/hr, and most preferably in the range of from about 500,000 Nl/kg/hr to about 30,000,000 Nl/kg/hr.

4. Combination Syngas Processes

Combination reforming processes can also be incorporated into this invention. Examples of combination reforming processes include autothermal reforming and fixed bed syngas generation. These processes involve a combination of gas phase partial oxidation and steam reforming chemistry.

The autothermal reforming process preferably comprises two syngas generating processes, a primary oxidation process and a secondary steam reforming process. In one embodiment, a hydrocarbon feed stream is steam reformed in a tubular primary reformer by contacting the hydrocarbon and steam with a reforming catalyst to form a hydrogen and carbon monoxide containing primary reformed gas, the carbon monoxide content of which is further increased in the secondary reformer. In one embodiment, the secondary reformer includes a cylindrical refractory lined vessel with a gas mixer, preferably in the form of a burner in the inlet portion of the vessel and a bed of nickel catalyst in the lower portion. In a more preferred embodiment, the exit gas from the primary reformer is mixed with air and residual hydrocarbons, and the mixed gas partial oxidized to carbon monoxides.

In another embodiment incorporating the autothermal reforming process, partial oxidation is carried out as the primary oxidating process. Preferably, hydrocarbon feed, oxygen, and optionally steam, are heated and mixed at an outlet of a single large coaxial burner or injector which discharges into a gas phase partial oxidation zone. Oxygen is preferably supplied in an amount which is less than the amount required for complete combustion.

Upon reaction in the partial oxidation combustion zone, the gases flow from the primary reforming process into the secondary reforming process. In one embodiment, the gases are passed over a bed of steam reforming catalyst particles or a monolithic body, to complete steam reforming. Desirably, the entire hydrocarbon conversion is completed by a single reactor aided by internal combustion.

In an alternative embodiment of the invention, a fixed bed syngas generation process is used to form syngas. In the fixed bed syngas generation process, hydrocarbon feed and oxygen or an oxygen-containing gas are introduced separately into a fluid catalyst bed. Preferably, the catalyst is comprised of nickel and supported primarily on alpha alumina.

The fixed bed syngas generation process is carried out at conditions of elevated temperatures and pressures that favor the formation of hydrogen and carbon monoxide when, for example, methane is reacted with oxygen and steam. Preferably, temperatures are in excess of about 1,700° F. (927° C.), but not so high as to cause disintegration of the catalyst or the sticking of catalyst particles together. Preferably, temperatures range from about 1,750° F. (954° C.) to about 1,950° F. (1,066° C.), more preferably, from about 1,800° F. (982° C.) to about 1,850° F. (1,010° C.).

Pressure in the fixed bed syngas generation process may range from atmospheric to about 40 atmospheres. In one embodiment, pressures of from about 20 atmospheres to about 30 atmospheres are preferred, which allows subsequent processes to proceed without intermediate compression of product gases.

In one embodiment of the invention, methane, steam, and oxygen are introduced into a fluid bed by separately injecting the methane and oxygen into the bed. Alternatively, each stream is diluted with steam as it enters the bed. Preferably, methane and steam are mixed at a methane to steam molar ratio of from about 1:1 to about 3:1, and more preferably from about 1.5:1 to about 2.5: 1, and the methane and steam mixture is injected into the bed. Preferably, the molar ratio of oxygen to methane is from about 0.2:1 to about 1.0:1, more preferably from about 0.4:1 to about 0.6:1.

In another embodiment of the invention, the fluid bed process is used with a nickel based catalyst supported on alpha alumina. In another embodiment, silica is included in the support. The support is preferably comprised of at least 95 wt % alpha alumina, more preferably at least about 98% alpha alumina, based on total weight of the support.

In one embodiment, a gaseous mixture of hydrocarbon feedstock and oxygen-containing gas are contacted with a reforming catalyst under adiabatic conditions. For the purposes of this invention, the term "adiabatic" refers to reaction conditions in which substantially all heat loss and radiation from the reaction zone are prevented, with the exception of heat leaving in the gaseous effluent stream of the reactor.

5. Converting Syngas to Methanol

The syngas is sent to a methanol synthesis process and converted to methanol. The methanol synthesis process is accomplished in the presence of a methanol synthesis catalyst.

In one embodiment, the syngas is sent as is to the methanol synthesis process. In another embodiment, the hydrogen, carbon monoxide, and/or carbon dioxide content of the syngas is adjusted for efficiency of conversion. Desirably, the syngas input to the methanol synthesis reactor has a molar ratio of hydrogen ($H_2$) to carbon oxides (CO+ $CO_2$) in the range of from about 0.5:1 to about 20:1, preferably in the range of from about 2:1 to about 10:1. In another embodiment, the syngas has a molar ratio of hydrogen ($H_2$) to carbon monoxide (CO) of at least 2:1. Carbon dioxide is optionally present in an amount of not greater than 50% by weight, based on total weight of the syngas.

Desirably, the stoichiometric molar ratio is sufficiently high so as maintain a high yield of methanol, but not so high as to reduce the volume productivity of methanol. Preferably, the syngas fed to the methanol synthesis has a stoichiometric molar ratio (i.e., a molar ratio of $H_2$:(2CO+ $3CO_2$)) of from about 1.0:1 to about 2.7:1, more preferably from about 1.1 to about 2.0, more preferably a stoichiometric molar ratio of from about 1.2:1 to about 1.8:1.

The $CO_2$ content, relative to that of CO, in the syngas should be high enough so as to maintain an appropriately high reaction temperature and to minimize the amount of undesirable by-products such as paraffins. At the same time, the relative $CO_2$ to CO content should not be too high so as to reduce methanol yield. Desirably, the syngas contains $CO_2$ and CO at a molar ratio of from about 0.5 to about 1.2, preferably from about 0.6 to about 1.0.

In one embodiment, the catalyst used in the methanol synthesis process includes an oxide of at least one element selected from the group consisting of copper, silver, zinc, boron, magnesium, aluminum, vanadium, chromium, manganese, gallium, palladium, osmium and zirconium. Preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

The methanol synthesis catalyst is made according to conventional processes. Examples of such processes can be found in U.S. Pat. Nos. 6,114,279; 6,054,497; 5,767,039; 5,045,520; 5,254,520; 5,610,202; 4,666,945; 4,455,394; 4,565,803; 5,385,949, with the descriptions of each being fully incorporated herein by reference.

In one embodiment, the syngas formed in the syngas conversion plant is cooled prior to being sent to the methanol synthesis reactor. Preferably, the syngas is cooled so as to condense at least a portion of the water vapor formed during the syngas process.

The methanol synthesis process implemented in the present invention can be any conventional methanol synthesis process. Examples of such processes include batch processes and continuous processes. Continuous processes are preferred. Tubular bed processes and fluidized bed processes are particularly preferred types of continuous processes.

In general, the methanol synthesis process takes place according to the following reactions:

$$CO + 2H_2 \rightarrow CH_3OH \quad (5)$$

$$CO_2 + 3H_2 \rightarrow CH_3OH + H_2O \quad (6)$$

The methanol synthesis process is effective over a wide range of temperatures. In one embodiment, the syngas is contacted with the methanol synthesis catalyst at a temperature in the range of from about 302° F. (150° C.) to about 842° F. (450° C.), preferably in a range of from about 347° F. (175° C.) to about 662° F. (350° C.), more preferably in a range of from about 392° F. (200° C.) to about 572° F. (300° C.).

The process is also operable over a wide range of pressures. In one embodiment, the syngas is contacted with the methanol synthesis catalyst at a pressure in the range of from about 15 atmospheres to about 125 atmospheres, preferably in a range of from about 20 atmospheres to about 100 atmospheres, more preferably in a range of from about 25 atmospheres to about 75 atmospheres.

Gas hourly space velocities vary depending upon the type of continuous process that is used. Desirably, gas hourly space velocity of flow of gas through the catalyst bed is in the range of from about 50 hr−1 to about 50,000 hr−1. Preferably, gas hourly space velocity of flow of gas through the catalyst bed is in the range of from about 250 hr−1 to about 25,000 hr−1, more preferably from about 500 hr−1 to about 10,000 hr−1.

The methanol synthesis process produces a variety of hydrocarbons as by-products. According to the methanol composition of this invention, it is desirable to operate the process so as to maximize not only the amount of methanol formed, but also aldehydes and other alcohols which are particularly desirable in the conversion of oxygenates to olefins. In is particularly appropriate to maximize the amount of methanol formed in the methanol synthesis, and remove hydrocarbons less desirable in the conversion of oxygenates to olefins from the crude methanol product stream formed in the methanol synthesis reactor.

6. Refining Crude Methanol to Make Methanol Product

In conventional methanol synthesis systems, the crude methanol product mixture formed in the methanol synthesis unit is further processed after reaction to obtain a desirable methanol-containing composition. Processing is accomplished by any conventional means. Examples of such means include distillation, selective condensation, and selective adsorption. Process conditions, e.g., temperatures and pressures, can vary according to the particular methanol composition desired. It is particularly desirable to minimize the amount of water and light boiling point components in the methanol-containing composition, but without substantially reducing the amount of methanol and desirable aldehydes and/or other desirable alcohols also present.

In one processing system, the crude methanol product from the methanol synthesis reactor is sent to a let down vessel so as to reduce the pressure to about atmospheric or slightly higher. This let down in pressure allows undesirable light boiling point components to be removed from the methanol composition as a vapor. The vapor is desirably of sufficient quality to use a fuel.

In another processing system, the crude methanol is sent from the methanol synthesizing unit to a distillation system. The distillation system contains one or more distillation columns which are used to separate the desired methanol composition from water and hydrocarbon by-products. Desirably, the methanol composition that is separated from the crude methanol comprises a majority of the methanol and a majority of aldehyde and/or alcohol supplements contained in the crude alcohol prior to separation. Preferably, the methanol composition that is separated from the crude methanol comprises a majority of the acetaldehyde and/or ethanol, if any, contained in the crude methanol prior to separation.

The distillation system optionally includes a step of treating the methanol steam being distilled so as to remove or neutralize acids in the stream. Preferably, a base is added in the system that is effective in neutralizing organic acids that are found in the methanol stream. Conventional base compounds can be used. Examples of base compounds include alkali metal hydroxide or carbonate compounds, and amine or ammonium hydroxide compounds. In one particular embodiment, about 20 ppm to about 120 ppm w/w of a base composition, calculated as stoichiometrically equivalent NaOH, is added, preferably about 25 ppm to about 100 ppm w/w of a base composition, calculated as stoichiometrically equivalent NaOH, is added.

The invention can include any distillation system that produces a "fusel oil" stream, which includes C1-C4 alcohols, ketones, aldehydes and water. The fusel oil stream has a boiling point higher than that of methanol. It is especially advantageous when the fusel oil stream is liquid taken from a column fed with the crude methanol from the let-down vessel or with the bottoms liquid from a column fed with such crude methanol, the off-take point being at a level below the feed level. Alternatively or additionally, the fusel oil stream is taken from a level above the feed level in such a column. Because some of the higher alcohols are advantageous in the methanol composition of this invention, it is desirable to operate the distillation system to recover the $C_2$-$C_4$ alcohols along with the methanol rather than in the fusel oil stream.

Examples of distillation systems include the use of single and two column distillation columns. Preferably, the single columns operate to remove volatiles in the overhead, methanol product at a high level, fusel oil as vapor above the feed and/or as liquid below the feed, and water as a bottoms stream.

In one embodiment of a two column system, the first column is a "topping column" from which volatiles or "light ends" are taken overhead and methanol liquid as bottoms. A non-limiting list of possible light ends includes hydrogen, carbon monoxide and methane. The second is a "refining column" from which methanol product is taken as an overhead stream or at a high level, and water is removed as a bottoms stream. In this embodiment, the refining column includes at least one off-take for fusel oil as vapor above the feed and/or as liquid below the feed.

In another embodiment of a two column system, the first column is a water-extractive column in which there is a water feed introduced at a level above the crude methanol feed level. It is desirable to feed sufficient water to produce a bottoms liquid containing over 40% w/w water, preferably 40% to 60% w/w water, and more preferably 80% to 95% w/w water. This column optionally includes one or more direct fusel oil side off-takes.

In yet another embodiment, the distillation system is one in which an aqueous, semi-crude methanol is taken as liquid above the feed in a single or refining column. The semi-crude methanol is passed to a refining column, from which methanol product is taken overhead or at a high level. Preferably, water or aqueous methanol is taken as a bottoms stream.

Alternatively, undesirable by-products are removed from the crude methanol stream from the methanol synthesis reactor by adsorption. In such a system, fusel oil can be recovered by regenerating the adsorbent.

An exemplary methanol synthesis system is illustrated in FIG. 1 and will now be described in greater detail. As shown in FIG. 1, a feed stream 95, which preferably includes natural gas, is directed to a desulfurization unit 97. Prior to entering the desulfurization unit 97, the feed stream 95 optionally is compressed by one or more compressors, not shown, to facilitate movement of the feed stream 95 and various intermediate streams through the methanol synthesis system. In one embodiment, the natural gas from feed stream 95 contacts water from water stream 96 in the desulfurization unit 97 in a countercurrent manner under conditions effective to remove sulfur-containing components, e.g., $H_2S$ and/or mercaptans, therefrom. In this manner, the desulfurization unit 97 acts as an absorption unit. Additionally or alternatively, the desulfurization unit 97 may act as an adsorption unit. In this embodiment, the desulfurization unit 97 preferably includes one or more columns that are packed with molecular sieve particles, e.g., 3-5 angstrom molecular sieve particles, the pores of which are adapted to selectively capture the sulfur-containing components from feed stream 95. The optional adsorption unit optionally includes a regeneration system, not shown, for regenerating deactivated or partially deactivated molecular sieve particles. If the desulfurization unit 97 includes an adsorption unit, the feed stream 95 preferably is heated to a temperature of between 700° F. (371° C.) and 800° F. (427° C.) by a heat exchanger, not shown, before it is directed to desulfurization unit 97. The desulfurization unit 97 forms desulfurized feed stream 100, which is directed to a reforming unit 101. Preferably, desulfurized feed stream 100 comprises less than 5 weight percent, more preferably less than 1 weight percent, and most preferably less than 0.01 weight percent sulfur-containing compounds, based on the total weight of the desulfurized feed stream 200.

The reforming unit 101 converts the natural gas in desulfurized feed stream 100 to syngas in syngas stream 98. Generally, the production of syngas involves a combustion reaction of natural gas, mostly methane, and an oxygen source, e.g., air, into hydrogen, carbon monoxide and/or carbon dioxide. Syngas production processes are well known, and include conventional steam reforming, autothermal reforming, or a combination thereof. Thus, reforming unit 101 may be a steam reforming unit, a partial oxidation unit, an autothermal reforming unit, and/or a combined reforming unit, e.g., a unit that combines two or more of these reforming processes. In one embodiment, water from water stream 96 preferably increases the water content of, and more preferably saturates, the feed stream 95, in the process of removing sulfur-containing components. Additionally or alternatively, the desulfurized feed stream 100 is directed to a separate saturization unit, not shown, in which water contacts the desulfurized feed stream 100 under conditions effective to saturate the desulfurized feed stream 100 or increase the water content thereof. For example, the saturization unit may include a packed or tray column wherein water contacts the desulfurized feed stream 100 in a countercurrent manner under conditions effective to saturate or increase the water content of the desulfurized feed stream 200. Saturation of the feed stream 95 and/or desulfurized feed stream 100 is particularly beneficial if the reforming unit 101 implements a steam reforming process as a water-containing or saturated desulfurized feed stream 100 may be necessary in order for the steam reforming process to convert the desulfurized feed stream 100 to syngas in syngas stream 98. Additionally or alternatively, water may be injected directly into the reforming unit 101, particularly if the reforming unit 101 provides a steam reforming process. Resulting syngas stream 98 is directed to a compression zone 99, wherein the syngas stream 98 is compressed in one or more stages to form compressed stream 102. Preferably, the compression zone 99 includes one or more centrifugal compressors. Compressed stream 102 is then directed to a methanol synthesis unit 105, wherein the syngas in compressed stream 102 contacts a methanol synthesis catalyst under conditions effective to convert at least a portion of the syngas to crude methanol in crude methanol stream 107. Optionally, unreacted syngas from methanol synthesis unit 105 is recycled to compression zone 99 as shown by unreacted syngas stream 92.

The crude methanol in crude methanol stream 107 includes light ends, methanol, water, and fusel oil. Preferably, prior to introduction into separation zone 94, the crude methanol stream 107 is treated with a caustic medium, not shown, in a caustic wash unit, not shown, under conditions effective to increase the pH of the crude methanol stream 107. As a result, the crude methanol stream 107 also optionally includes dissolved caustic salts. As shown, crude methanol stream 107 is directed to a separation zone 49, which is adapted to separate one or more of these components and isolate a relatively pure methanol stream. The separation zone 94 includes a light ends separation unit 110, such as a topping column, and a refining column 113. Crude methanol stream 107 is first directed to the light ends separation unit 110, wherein conditions are effective to separate the crude methanol stream 107 into light ends stream 111 and bottoms crude methanol stream 112, which contains methanol, water, fusel oil, and optionally dissolved caustic salts. The light ends separation unit 110 typically includes from about 50 to about 80 trays and has a cross-sectional diameter of from about 8 feet (2.4 m) to about 20 feet (6 m). At least a portion of the light ends stream 111 preferably is recycled to methanol synthesis unit 105, as shown, for further conversion to methanol while the bottoms crude methanol stream 112 is directed to refining column 113 for further processing. In refining column 113, the bottoms crude methanol stream 112 is subjected to conditions effective to separate the bottoms crude methanol stream 112 into a refined methanol stream 114, a fusel oil stream 93, and a water stream 115. A majority of the caustic salts, if any, from bottoms crude methanol stream 112 are dissolved in water stream 115. Preferably, refined methanol stream 114 contains at least 90 weight percent, more preferably at least 95 weight percent and most preferably at least 99 weight percent methanol, based on the total weight of the refined methanol stream 114. Preferably, refined methanol stream 114 contains less than 5.0 weight percent, more preferably less than 1.0 weight percent and most preferably less than 0.25 weight percent water, based on the total weight of the refined methanol stream 114. The refining column 113 typically includes from about 80 to about 120 trays and has a cross-sectional diameter of from about 10 feet (3.0 m) to about 24 feet (7.2 m).

C. Fuel Alcohol Synthesis Systems

As indicated above, the present invention, in one embodiment, provides for a combined process for forming methanol and fuel alcohol and converting the methanol and fuel alcohol to light olefins in an OTO reaction system. A non-limiting description of several fuel alcohol synthesis systems that may be incorporated into the present invention will now be described.

As with methanol synthesis, there are numerous technologies available for producing fuel alcohol. The preferred embodiment for forming fuel alcohol according to the present invention comprises the reaction of carbon monoxide, hydrogen and optionally carbon dioxide in the presence of a fuel alcohol synthesis catalyst to form fuel alcohol and water. The synthesis of fuel alcohol occurs in a fuel alcohol synthesis zone. Without limiting the invention to a particular reaction mechanism, the synthesis of fuel alcohol may be illustrated as follows:

$$nCO + 2nH_2 \rightarrow C_nH_{2n+1}OH + (n-1)H_2O \qquad (7)$$
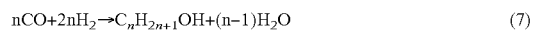

where n is a whole number.

According to the present invention, the fuel alcohol synthesis reaction or reactions optionally are catalyzed using a fuel alcohol synthesis catalyst, preferably containing a metal atom, optionally with a halogen promoter. Many metal compounds and promoters can be used. Optionally, secondary activators or ligands may be used in conjunction with the metal catalysts and promoters. These secondary activators can be other metallic salts or compounds, amines, phosphorus compounds, as well as a multitude of other compounds that have been disclosed in the published literature. Thus, a typical catalyst system for the synthesis of fuel alcohol comprises a metal atom-containing catalyst, a promoter and optionally ligands, solvents and/or secondary activators.

A variety of references disclose the synthesis of fuel alcohol from syngas. See, for example, (i) El Sawy, A. H., *DOE report DE*90010325 and references therein, the entireties of which are incorporated herein by reference; (ii) Courty, Charmette, Raimbault and Travers, *Rev. De Institute du Petrole*, vol. 45(4), 561-578 (1990), the entireties of which are incorporated herein by reference; and (iii) Klier, Herman, Simmons and Lyman, *DOE report DE*89009888 and references therein, the entireties of which are incorporated herein by reference.

Fuel alcohol synthesis may occur at a variety of reaction conditions. In one embodiment, the fuel alcohol synthesis reaction temperature in the fuel alcohol synthesis zone ranges from about 200° C. to about 500° C., preferably from about 250° C. to about 450° C., and most preferably from about 300° C. to about 400° C. The pressure in the fuel alcohol synthesis zone also may vary widely, although the pressure preferably is in the range of the pressure of the syngas that is directed to the methanol synthesis unit, discussed above. Optionally, the pressure in the fuel alcohol synthesis zone ranges from about 5 to about 20 MPa, preferably from about 6 to about 18 MPa, and most preferably from about 10 to about 15 MPa.

Although many different fuel alcohol synthesis catalysts may be utilized in the fuel alcohol synthesis zone to facilitate conversion of the syngas contained therein to fuel alcohol, the fuel alcohol synthesis catalyst preferably comprises a microporous zeolitic material. Thus, in one embodiment, the fuel alcohol is formed by contacting syngas with a fuel alcohol synthesis catalyst comprising a microporous zeolitic material under conditions effective to convert the syngas to fuel alcohol, which is contained in a fuel alcohol-containing stream.

Additionally or alternatively, the fuel alcohol synthesis catalyst comprises copper and an oxide of zinc. Additionally, in this embodiment, the fuel alcohol synthesis catalyst preferably comprises an oxide of one or both of chromium and/or aluminum. Specifically, in this embodiment, the fuel alcohol synthesis catalyst preferably comprises one or more of $Cu/ZnO/Cr_2O_3$ and $Cu/ZnO/Al_2O_3$. In this embodiment, it is preferred that the fuel alcohol synthesis catalyst is alkali promoted. Thus, the fuel alcohol optionally is formed in this aspect of the invention by contacting syngas with a fuel alcohol synthesis catalyst comprising one or more of $Cu/ZnO/Cr_2O_3$ and $Cu/ZnO/Al_2O_3$, which fuel alcohol synthesis catalyst optionally is alkali promoted, under conditions effective to convert the syngas to the fuel alcohol.

Additionally or alternatively, the fuel alcohol synthesis catalyst comprises an oxide of one or more of zinc, chromium, copper, cobalt, and nickel. In this embodiment, it is preferred that the fuel alcohol synthesis catalyst is alkali, lanthanum or cerium promoted. Thus, the fuel alcohol optionally is formed in this aspect of the invention by contacting syngas with a fuel alcohol synthesis catalyst under conditions effective to convert the syngas to the fuel alcohol, wherein the fuel alcohol synthesis catalyst comprises an oxide of one or more of zinc, chromium, copper, cobalt, and nickel, which fuel alcohol synthesis catalyst optionally is alkali, lanthanum or cerium promoted.

Additionally or alternatively, the fuel alcohol synthesis catalyst comprises a compound comprising molybdenum and preferably sulfur. In this embodiment, it is preferred that the fuel alcohol synthesis catalyst is alkali promoted. Specifically, the fuel alcohol optionally is catalyzed by one or more of $MoS_2$ and $Co/MoS_2$. Thus, the fuel alcohol can be formed by contacting syngas with a fuel alcohol synthesis catalyst under conditions effective to convert the syngas to the fuel alcohol, wherein the fuel alcohol synthesis catalyst comprises one or more of $MoS_2$ and $Co/MoS_2$, and wherein the fuel alcohol synthesis catalyst optionally is alkali promoted.

The alkali metal atom component of the catalyst system can come from any of the known ionic compounds of the alkali metals sodium, potassium, lithium, rubidium and cesium. Preferred alkali metal atom components are derived from sodium salts and potassium salts. Illustrative sources thereof include sodium iodide, sodium bicarbonate, sodium carbonate, sodium nitrate, sodium nitrite, sodium sulfate, sodium bisulfate, sodium chromate, sodium permanganate, sodium chlorate, sodium persulfate, sodium tetraborate, sodium bromide, sodium chloride, sodium fluoride, sodium sulfite, sodium hypochlorite, as well as any other ionic salt of sodium. Rather than repeat the individual compound names, the corresponding potassium, lithium, rubidium and cesium salts are illustrative of useful ionic compounds.

The concentration of alkali metal atoms in the fuel alcohol synthesis zone optionally is from about 0.00013 to about 1 mole per liter; preferably from about 0.07 to about 0.6 mole per liter.

Preferably, hydrogen and carbon monoxide are present in the syngas that is directed to the fuel alcohol synthesis zone. The molar ratio of $H_2$:CO in the syngas that is directed to the fuel alcohol synthesis zone can vary from about 20:1 to about 1:20, from about 10:1 to about 1:10, and preferably from about 3:1 to about 1:3. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

According to the present invention, a fuel alcohol-containing stream is formed, which comprises the fuel alcohol. The fuel alcohol-containing stream preferably comprises two or more alcohols in the C2 to C5 range. Higher alcohols and carboxylic acid esters may also be formed while carrying out the process of this invention. For example, the fuel alcohol-containing stream may include methyl formate, methyl acetate, ethyl acetate, ethyl ether. The major by-products of the process such as the higher molecular weight alcohols and carboxylic acid esters, are, of course, also useful compounds and major articles of commerce. The higher alcohols, the carboxylic acid esters and ethers can easily be separated from one another by conventional means, e.g., fractional distillation in vacuo, if desired.

The precise amount and type of components contained in the fuel alcohol-containing stream will vary widely depending on catalyst type, reaction conditions, and syngas composition used. For example, Table I, below, provides three catalyst systems and indicates exemplary product yields and operating conditions. See El Sawy, A. H., DOE report DE90010325, pp. 3-17, 3-18.

TABLE I

Product Yields (Wt. %) and Reaction Conditions of Three Fuel Alcohol Synthesis Systems

| Process Product Slate | Main Catalyst Constituents | | |
|---|---|---|---|
| (anhydrous basis) | Cu/Co/Al | Zn/Cr/K | Cu/ZnO/Al |
| Methanol | 57.5 | 70.0 | 64.5 |
| Ethanol | 28.5 | 2.5 | 11.5 |
| C3 alcohols | 7.1 | 3.4 | 5.2 |
| C4 alcohols | 2.8 | 12.5 | 7.4 |
| C5+ alcohols | 2.5 | 9.5 | 7.4 |
| Hydrocarbons | 0.3 | — | 0.02 |
| Esters | 0.7 | 0.1 | 0.8 |
| Other Oxygenated Products | 0.6 | 2.0 | 3.18 |
| Total Alcohols | 98.4 | 97.9 | 96.0 |
| Operating T (° C.) | 260-320 | 350-420 | 285-300 |
| Operating Pressure (MPa) | 6-10 | 10-18 | 6-9 |
| Syngas Feed Ratio ($H_2$:CO) | 2.0-2.5 | 1.5-2 | 0.5-1 |
| Syngas $CO_2$ Content (Vol. %) | 0.5-3.0 | 2-6 | 1.0 |

As indicated by Table I, the amount of ethanol contained in the fuel alcohol-containing stream may vary. The fuel alcohol-containing stream preferably comprises at least about 10 weight percent ethanol, more preferably at least about 25 weight percent ethanol and most preferably at least about 35 weight percent ethanol, based on the total weight of the fuel alcohol-containing stream. In terms of ranges, the fuel alcohol-containing stream optionally comprises on the order of from about 5 to about 60 weight percent ethanol, preferably from about 10 to about 50 weight percent ethanol, and most preferably from about 20 to about 40 weight percent ethanol, based on the total weight of the fuel alcohol-containing stream.

The fuel alcohol-containing stream also comprises one or more C3 alcohols, preferably on the order of from about 5 to about 80 weight percent C3 alcohols, preferably from about 10 to about 60 weight percent C3 alcohols, and most preferably from about 15 to about 40 weight percent C3 alcohols, based on the total weight of the fuel alcohol-containing stream. Optionally, the C3 alcohols comprise one or more of 1-propanol, 2-propanol, and/or 1,2-propadiol.

Additionally or alternatively, the fuel alcohol-containing stream comprises one or more C4 alcohols, preferably on the order of from about 0.1 to about 20 weight percent C4 alcohols, preferably from about 1 to about 10 weight percent C4 alcohols, and most preferably from about 2 to about 5 weight percent C4 alcohols, based on the total weight of the fuel alcohol-containing stream. Optionally, the C4 alcohols comprise one or more of 1-butanol; 2-butanol; 1,4-butanediol; 1,3-butanediol; 1,2-butanediol; isobutyl alcohol; sec-butyl alcohol; and t-butyl alcohol.

The fuel alcohol-containing stream preferably comprises at least about 5 weight percent C3-C4 alcohols, more preferably at least about 10 weight percent C3-C4 alcohols, and most preferably at least about 15 weight percent C3-C4 alcohols.

Optionally, the fuel alcohol-containing stream comprises one or more C5 alcohols, preferably on the order of from about 0.01 to about 10 weight percent C5 alcohols, preferably from about 0.1 to about 5 weight percent C5 alcohols, and most preferably from about 0.1 to about 3 weight percent C5 alcohols, based on the total weight of the fuel alcohol-containing stream. Optionally, the C5 alcohols comprise one or more of 1-pentanol; 2-pentanol; 3-pentanol; 1,5-pentanediol; 1,4-pentanediol; 1,3-pentanediol; and 1,2-pentanediol.

Additionally, the fuel alcohol-containing stream optionally comprises one or more C6+ alcohols, preferably on the order of from about 0.01 to about 10 weight percent C6+ alcohols, preferably from about 0.1 to about 5 weight percent C6+ alcohols, and most preferably from about 0.1 to about 3 weight percent C6+ alcohols, based on the total weight of the fuel alcohol-containing stream.

Ideally, the fuel alcohol-containing stream contains low amounts of methanol, if any. Preferably, the fuel alcohol-containing stream comprises less than 75 weight percent methanol, more preferably less than 65 weight percent methanol, and most preferably less than 60 weight percent methanol, based on the total weight of the fuel alcohol-containing stream.

In terms of weight ratios, if the fuel alcohol-containing stream comprises methanol and ethanol, then the weight ratio of methanol to ethanol ranges from about 1 to about 6, more preferably from about 1.5 to about 5, and most preferably from about 2 to about 4. If the fuel alcohol-containing stream comprises ethanol and C3 alcohols, then the weight ratio of ethanol to C3 alcohols preferably ranges from about 1 to about 30, more preferably from about 5 to about 30, and most preferably from about 10 to about 20.

The novel process of this invention can be conducted in a batch, semi-continuous or continuous fashion. The catalyst may be initially introduced into the fuel alcohol synthesis zone batchwise, or it may be continuously or intermittently introduced into such a zone during the course of the synthesis reaction. Operating conditions can be adjusted to optimize the formation of the fuel alcohol product, and after recovery of the alcohol and other products, a fraction rich in the catalyst composition may then be recycled to the reaction zone, if desired, and additional products generated. A non-limiting list of preferred reactor types for the synthesis of fuel alcohol includes fixed bed, slurry reactors and fluid bed reactors.

One can additionally have an inert solvent present in the reaction mixture. A wide variety of substantially inert solvents are useful in the process of this invention including hydrocarbon and oxygenated hydrocarbon solvents. Suitable oxygenated hydrocarbon solvents are compounds comprising carbon, hydrogen and oxygen and those in which the only oxygen atoms present are in ether groups, ester groups, ketone carbonyl groups or hydroxyl groups of alcohols. Generally, the oxygenated hydrocarbon will contain 3 to 12 carbon atoms and preferably a maximum of 3 oxygen atoms. The solvent preferably is substantially inert under reaction conditions, is relatively non-polar and has a normal boiling point of at least 65° C. at atmospheric pressure, and preferably, the solvent will have a boiling point greater than that of ethanol and other oxygen-containing reaction products so that recovery of the solvent by distillation is facilitated.

Preferred ester type solvents are the aliphatic and acylic carboxylic acid monoesters as exemplified by butyl acetate, methyl benzoate, isopropyl iso-butyrate, and propyl propionate as well as dimethyl adipate. Useful alcohol-type solvents include monohydric alcohols such as cyclohexanol, 1-hexanol, 2-hexanol, neopentanol, 2-octanol, etc. Suitable ketone-type solvents include, for example, cyclic ketones such as cyclohexanone, 2-methylcyclohexanone, as well as acylic ketones such as 2-pentanone, butanone, acetophenone, etc. Ethers that may be utilized as solvents include cyclic, acyclic and heterocyclic materials. Preferred ethers are the heterocyclic ethers as illustrated by 1,4-dioxane and 1,3-dioxane. Other suitable ether solvents include isopropyl propyl ether, diethylene glycol dibutyl ether, dibutyl ether, ethyl butyl ether, diphenyl ether, heptyl phenyl ether, anisole, tetrahydrofuran, etc. The most useful solvents of all of the above groups include the ethers as represented by monocyclic, heterocyclic ethers such a 1,4-dioxane or p-dioxane, etc. Hydrocarbon solvents, such as hexane, heptane, decane, dodecane, tetradecane, etc. are also suitable solvents for use in this invention. In the practice of this invention, it is also possible to add a small amount of water to the solvent and still obtain satisfactory results.

The reaction time varies depending upon the reaction parameters, reactor size and charge, and the individual components employed at the specific process conditions.

D. OTO Reaction Systems

The present invention, in one embodiment, provides for combining a methanol synthesis system with a fuel alcohol synthesis system and an OTO reaction system, which is discussed in more detail hereinafter. As used herein, "reaction system" means a system comprising a reaction zone, optionally a disengaging zone, optionally a catalyst regenerator, optionally a catalyst cooler and optionally a catalyst stripper.

Typically, molecular sieve catalysts have been used to convert oxygenate compounds to light olefins. Optionally, the molecular sieve catalyst composition comprises a zeolitic molecular sieve catalyst composition. Ideally, the molecular sieve catalyst composition comprises an alumina or a silica-alumina catalyst composition. Silicoaluminophosphate (SAPO) molecular sieve catalysts are particularly desirable in such conversion processes, because they are highly selective in the formation of ethylene and propylene. A non-limiting list of preferable SAPO molecular sieve catalyst compositions includes SAPO-17, SAPO-18, SAPO-34, SAPO-35, SAPO-44, the substituted forms thereof, and mixtures thereof. Preferably, the molecular sieve catalyst composition comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

Although the present application is specifically directed to combining a methanol/fuel alcohol synthesis system with an OTO reaction system, one or more additional components may be included in the feedstock that is directed to the OTO reaction system. For example, the feedstock that is directed to the OTO reaction system optionally contains, in addition to methanol and fuel alcohol, one or more aliphatic-containing compounds such as alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and more preferably from 1 to 4 carbon atoms, and most preferably methanol.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as DME, diethyl ether and methylethyl ether, alkyl-halides such as methyl chloride and ethyl chloride, alkyl ketones such as dimethyl ketone, alkyl-aldehydes such as formaldehyde and acetaldehyde, and various acids such as acetic acid.

In a preferred embodiment of the process of the invention, the feedstock contains one or more oxygenates in addition to methanol and fuel alcohol or, more specifically, one or more organic compounds containing at least one oxygen atom. In the most preferred embodiment of the process of invention, the oxygenate in the feedstock (in addition to methanol and ethanol) comprises one or more alcohols, preferably aliphatic alcohols where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates, in addition to methanol and ethanol, include n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock comprises methanol, ethanol and one or more of DME, diethyl ether or a combination thereof.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene-, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomers include unsaturated monomers, diolefins having 4 to 18 carbon atoms, conjugated or nonconjugated dienes, polyenes, vinyl monomers and cyclic olefins.

In a preferred embodiment, the feedstock, which contains methanol and fuel alcohol, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as an oxygenate to olefins (OTO) reaction process. In an OTO process, typically an oxygenated feedstock, most preferably a methanol- and fuel alcohol-containing feedstock, is converted in the presence of a molecular sieve catalyst composition into one or more olefins, preferably and predominantly, ethylene and/or propylene, referred to herein as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically, the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 hr−1 to about 5000 hr−1, preferably from about 2 hr−1 to about 3000 hr−1, more preferably from about 5 hr−1 to about 1500 hr−1, and most preferably from about 10 hr−1 to about 1000 hr−1. In one preferred embodiment, the WHSV is greater than 20 hr−1, preferably the WHSV for conversion of a feedstock containing methanol, DME, or both, is in the range of from about 20 hr−1 to about 300 hr−1.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

E. Integrated Reaction System

As indicated above, in one embodiment, the present invention is directed to a process for forming an alcohol-containing stream, which comprises methanol and fuel alcohol. The methanol is synthesized in a methanol synthesis unit, and the fuel alcohol is synthesized in a fuel alcohol synthesis unit, which preferably includes a fuel alcohol synthesis zone. The alcohol-containing stream is particularly suitable for use in an OTO reaction system. Thus, in one embodiment, the present invention is directed to a system for producing light olefins, which system comprises a methanol synthesis unit, a fuel alcohol synthesis unit and an OTO reaction system.

In one embodiment, the invention is to a process for producing light olefins. The process includes a step of providing an alcohol-containing stream comprising methanol, ethanol, one or more C3 alcohols and one or more C4 alcohols. At least a portion of the alcohol-containing stream contacts a molecular sieve catalyst composition in a reaction zone under conditions effective to form ethylene and propylene. Preferably, the ethylene and propylene are yielded in an effluent stream having an ethylene to propylene weight ratio of greater than 1.0. In terms of ranges, the ethylene to propylene weight ratio preferably is from about 1.1 to about 2.5, and most preferably from about 1.2 to about 1.5.

Optionally, the process further comprises a step of separating a majority of the ethylene from a majority of the propylene to form an ethylene-containing stream and a propylene-containing stream. The ethylene-containing stream optionally contacts a polymerization catalyst under conditions effective to convert at least a portion of the ethylene contained therein to polyethylene. Additionally or alternatively, the propylene-containing stream contacts a polymerization catalyst under conditions effective to convert at least a portion of the propylene contained therein to polypropylene.

The process optionally comprises a step of providing a methanol-containing stream comprising the methanol, providing a fuel alcohol-containing stream comprising the ethanol, the C3 alcohol and the C4 alcohol, and combining the methanol-containing stream and the fuel alcohol-containing stream to form the alcohol-containing stream.

The precise composition of the alcohol-containing stream may vary so long as the alcohol-containing stream comprises methanol, ethanol, one or more C3 alcohols and one or more C4 alcohols. Ideally, the alcohol-containing stream comprises less than 90 weight percent methanol, optionally less than 85 weight percent methanol, or less than 80 weight percent methanol, based on the total weight of the alcohol-containing stream. In terms of ranges, the alcohol-containing stream optionally comprises from about 80 to about 96 weight percent methanol, preferably from about 84 to about 92 weight percent methanol, more preferably from about 86 to about 90 weight percent methanol, and most preferably about 88 weight percent methanol, based on the total weight of the alcohol-containing stream.

The alcohol-containing stream preferably comprises at least about 5 weight percent ethanol, more preferably at least about 10 weight percent ethanol and most preferably about 12 weight percent ethanol, based on the total weight of the alcohol-containing stream. In terms of ranges, the alcohol-containing stream optionally comprises from about 6 to about 18 weight percent ethanol, preferably from about 8 to about 16 weight percent ethanol, and most preferably from about 10 to about 14 weight percent ethanol, based on the total weight of the alcohol-containing stream.

The alcohol-containing stream optionally comprises less than 15, preferably less than 10 and most preferably less than 5 weight percent C3 alcohols, based on the total weight of the alcohol-containing stream. In terms of lower range limitations, the alcohol-containing stream optionally comprises more than 1 weight percent, more than 2 weight percent or more than 4 weight percent C3 alcohols, based on the total weight of the alcohol-containing stream. In terms of ranges, the alcohol-containing stream optionally comprises from about 1.7 to about 27 weight percent, from about 3.3 to about 20 weight percent, or from about 5 to about 13.3 weight percent C3 alcohols, based on the total weight of the alcohol-containing stream.

The alcohol-containing stream preferably comprises less than 5, more preferably less than 3 and most preferably less than 1 weight percent C4 alcohols, based on the total weight of the alcohol-containing stream. In terms of lower range limitations, the alcohol-containing stream optionally comprises more than 10 wppm, more than 100 wppm or more than 500 wppm C4 alcohols, based on the total weight of the alcohol-containing stream. In terms of ranges, the alcohol-containing stream optionally comprises from about 0.03 to about 7 weight percent, from about 0.3 to about 3.3 weight percent, or from about 0.7 to about 1.7 weight percent C4 alcohols, based on the total weight of the alcohol-containing stream. The methanol to C2-C4 alcohol weight ratio of the alcohol-containing stream preferably is from about 0.1 to about 4.0, and more preferably from about 0.33 to about 3.0.

In another embodiment, the invention is to a process for producing light olefins from syngas. In this process, the invention includes a step of contacting a first syngas stream comprising carbon monoxide, carbon dioxide and hydrogen with a methanol synthesis catalyst under first conditions effective to form a methanol-containing stream comprising methanol and water. A second syngas stream comprising carbon monoxide, carbon dioxide and hydrogen contacts a fuel alcohol synthesis catalyst under second conditions effective to form a fuel alcohol-containing stream comprising ethanol, propanol and butanol. The two above-described contacting steps preferably occur in parallel to one another. At least a portion of the methanol-containing stream is combined with at least a portion of the fuel alcohol-containing stream to form a combined stream. At least a portion of the combined stream contacts a molecular sieve catalyst composition in a reaction zone under third conditions effective to form ethylene and propylene.

In this embodiment, the alcohol-containing stream optionally comprises methanol, fuel alcohol and water. Thus, the molecular sieve catalyst compositions utilized to convert oxygenates to light olefins may be able to tolerate a certain amount of water in the alcohol-containing stream. To increase reactor efficiency, however, it is preferred to remove a weight majority of the water from the alcohol-containing stream before the alcohols in the alcohol-containing stream contact the molecular sieve catalyst composition under conditions effective to convert the alcohols to light olefins. Thus, the alcohol-containing stream optionally comprises less than about 3 weight percent water, more preferably less than about 1 weight percent water and most preferably less than about 0.2 weight percent water.

The alcohol-containing stream also may include light ends such as carbon monoxide, methane and hydrogen. If so, then the process preferably includes a step of removing at least a portion, preferably a weight majority, of the light ends from at least a portion of the alcohol-containing stream.

In one embodiment of the present invention, the process of converting the methanol and the fuel alcohol in the presence of a molecular sieve catalyst composition to the light olefins also produces carbon monoxide. In this embodiment, the carbon monoxide optionally is separated from the light olefins. The separated carbon monoxide then may be directed to the methanol synthesis zone and/or the fuel alcohol synthesis zone to provide a carbon monoxide source for converting the syngas to methanol or for converting the syngas to fuel alcohol.

Similarly, in one embodiment of the present invention, the process of converting the methanol and the fuel alcohol in the presence of a molecular sieve catalyst composition to the light olefins also produces hydrogen. In this embodiment, the hydrogen optionally is separated from the light olefins. The separated hydrogen then may be directed to the methanol synthesis zone and/or to the fuel alcohol synthesis zone to provide a hydrogen source for the step of converting the syngas to methanol or for converting the syngas to fuel alcohol.

Optionally, the process further includes steps of forming the syngas (e.g., one or both the first and the second syngas streams) from natural gas. For example, the process optionally includes a step of contacting a natural gas stream with oxygen under fourth conditions effective to convert the natural gas stream into an initial syngas stream. The initial syngas stream may be separated to form the first syngas stream and the second syngas stream.

In another embodiment, the invention is to a process for producing an alcohol mixture suitable for use as a feedstock for an oxygenate to olefin reaction system. In this embodiment, the invention includes a step of contacting a first syngas stream comprising carbon monoxide, carbon dioxide and hydrogen with a methanol synthesis catalyst under first conditions effective to form a methanol-containing stream comprising methanol and water. A second syngas stream comprising carbon monoxide, carbon dioxide and hydrogen contacts a fuel alcohol synthesis catalyst under second conditions effective to form a fuel alcohol-containing stream comprising ethanol, propanol and butanol. At least a portion of the methanol-containing stream is combined with at least a portion of the fuel alcohol-containing stream to form a combined stream, which preferably has a methanol to C2-C4 alcohol weight ratio of from about 0.1 to about 4.0, preferably from about 0.33 to about 3.0, and most preferably from about 0.5 to about 1.0. A weight majority of the water optionally is removed from the combined stream to form a dry combined stream. The dry combined stream preferably comprises less than 10 weight percent, preferably less than 5 weight percent, and most preferably less than 2 weight percent water, based on the total weight of the dry combined stream. This embodiment optionally includes a step of directing the combined stream, or a portion thereof (either an aliquot or a non-aliquot portion), to an OTO reaction system.

In yet another embodiment, the invention is to a process for producing light olefins from syngas. The invention includes a step of contacting a first syngas stream comprising carbon monoxide, carbon dioxide and hydrogen with a methanol synthesis catalyst under first conditions effective to form a methanol-containing stream comprising methanol and water. A second syngas stream comprising carbon monoxide, carbon dioxide and hydrogen contacts a fuel alcohol synthesis catalyst under second conditions effective to form a fuel alcohol-containing stream comprising ethanol, propanol and butanol. At least a portion of the methanol-containing stream is combined with at least a portion of the fuel alcohol-containing stream to form a combined stream. At least a portion of the combined stream contacts a molecular sieve catalyst composition in a reaction system under third conditions effective to convert the methanol, the ethanol, optionally the propanol and optionally the butanol to light olefins. An effluent stream is yielded from the reaction system, which effluent stream comprises ethylene and propylene and has an ethylene to propylene weight ratio of from about 0.9 to about 3.0, preferably from about 1.1 to about 2.5, and most preferably from about 1.2 to about 1.5.

Optionally, the fuel alcohol synthesis zone is made part of an existing methanol synthesis system. In this embodiment, the beds in the methanol synthesis unit preferably are replaced with beds suitable for the fuel alcohol synthesis. Reactor beds preferred over fixed bed methanol reactors include fuel alcohol slurry beds and/or fluid beds. Additionally or alternatively, a second fuel alcohol synthesis unit having a fuel alcohol synthesis zone can be incorporated into a methanol synthesis system, as described below with reference to FIGS. 2-3.

Figure 2:
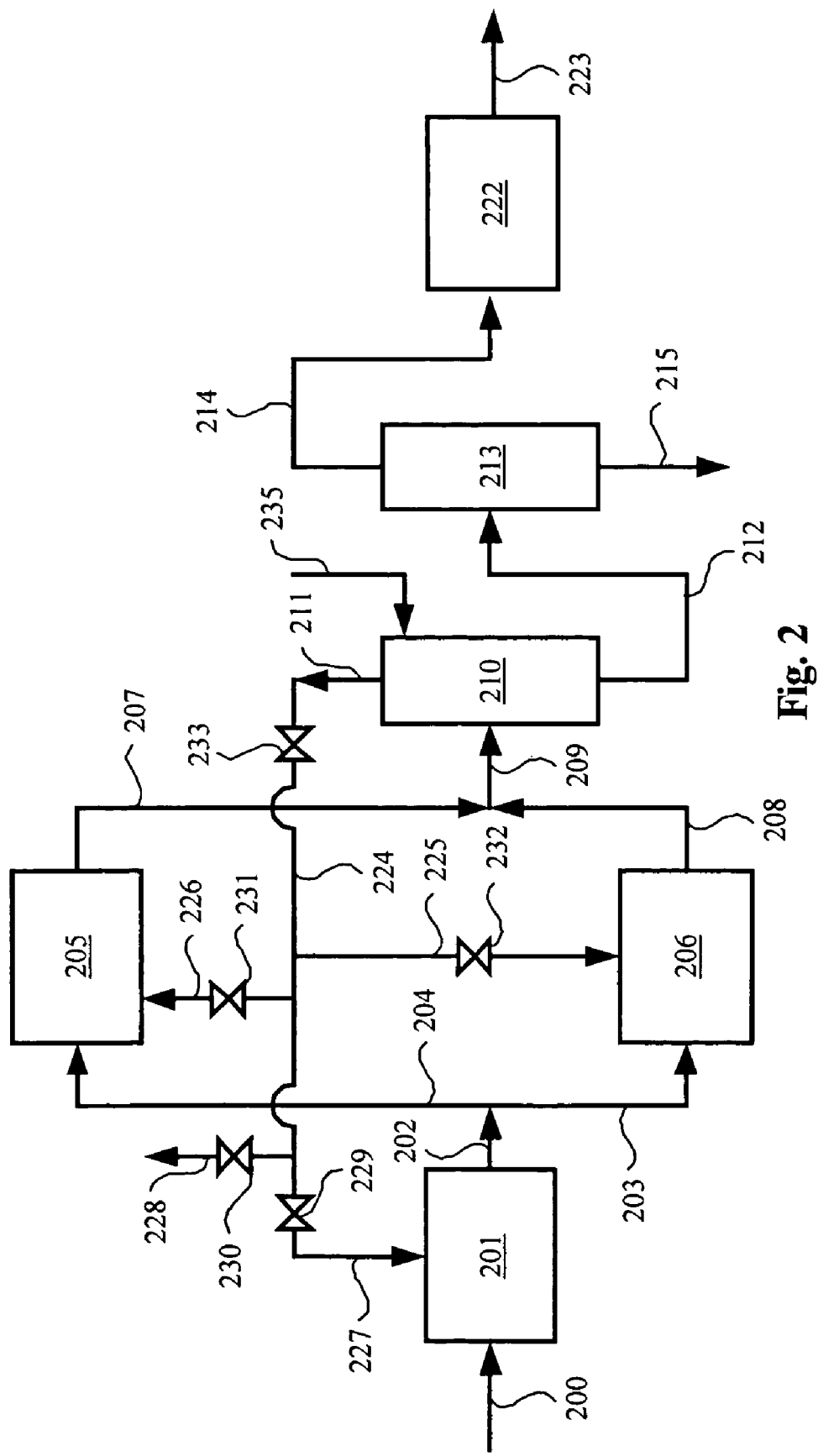
FIG. 2 is a flow diagram of one embodiment of the present invention.
Figure 3:
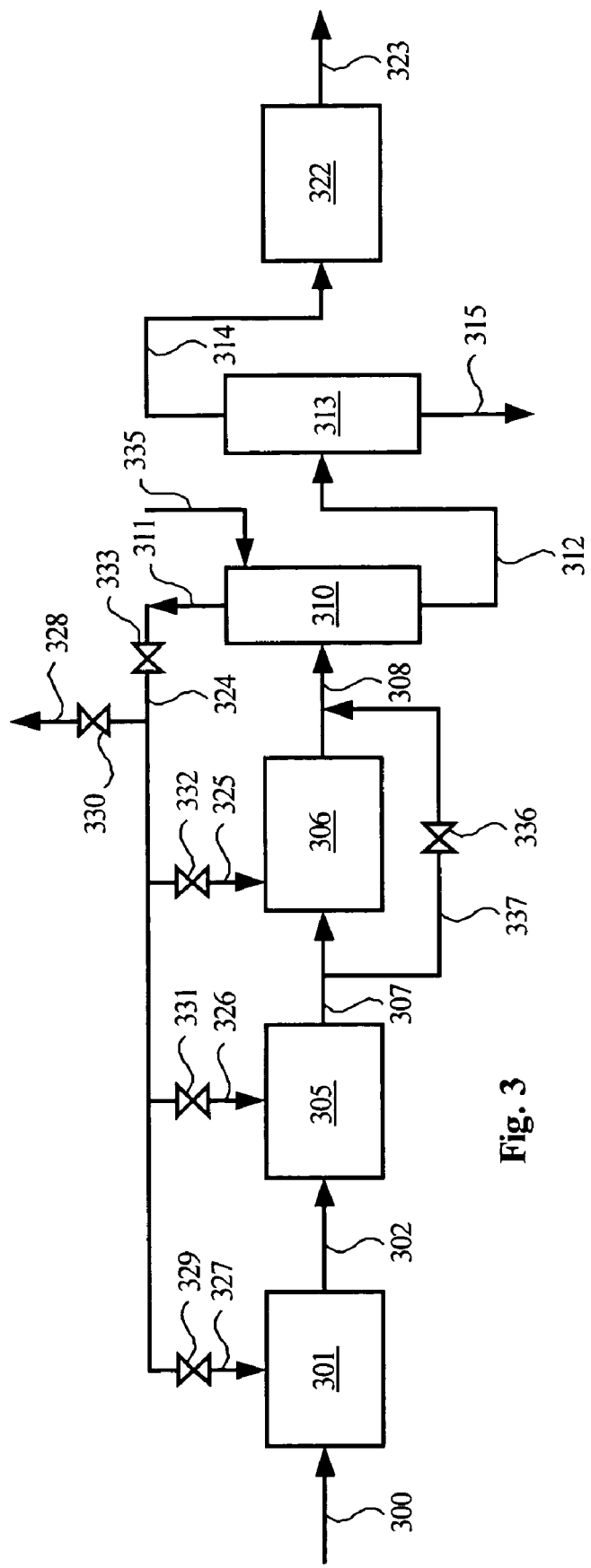
FIG. 3 is a flow diagram of another embodiment of the present invention.

FIGS. 2-3 of the present specification illustrate two non-limiting examples of integrated systems according to two embodiments of the present invention.

FIG. 2 illustrates one embodiment of the present invention wherein the methanol synthesis unit operates in parallel to the fuel alcohol synthesis unit. As shown, a natural gas stream 200 comprising natural gas is directed to a syngas generation unit 201. Ideally, the natural gas stream 200 comprises less than 5 weight percent, more preferably less than 1 weight percent, and most preferably less than 0.01 weight percent sulfur-containing compounds, based on the total weight of the natural gas stream 200. In the syngas generation unit 201, the natural gas in natural gas stream 200 contacts oxygen under conditions effective to convert the natural gas into syngas, which is yielded from the syngas generation unit 201 in syngas stream 202. Generally, the production of syngas involves a combustion reaction of natural gas, mostly methane and an oxygen source, e.g., air, into hydrogen, carbon monoxide and/or carbon dioxide. Syngas production process are well known, and include conventional steam reforming, autothermal reforming, or a combination thereof. Thus, syngas generation unit 201 may be a steam reforming unit, a partial oxidation unit, an autothermal reforming unit, and/or a combined reforming unit, e.g., a unit that combines two or more of these reforming processes. Optionally, water from a water stream, not shown, is added to the natural gas stream 200 or the syngas generation unit 201 in order to increase the water content of, and preferably saturate, the natural gas stream 200. Natural gas stream 200 optionally is desulfurized and/or saturated by any of the methods described above with reference to FIG. 1.

Syngas stream 202 ideally is compressed in one or more compressors, not shown, and is divided into a first derivative syngas stream 204 and a second derivative syngas stream 203. Optionally, the syngas in first derivative syngas stream 204 is compressed to provide ideal pressurization characteristics for methanol synthesis. Similarly, second derivative syngas stream 203 optionally is compressed to provide ideal pressurization characteristics for conversion thereof to fuel alcohol in fuel alcohol synthesis unit 206. First derivative syngas stream 204, or a portion thereof, is directed to a methanol synthesis unit 205 wherein the syngas in first derivative syngas stream 204 contacts a methanol synthesis catalyst under conditions effective to convert the syngas to methanol. Thus, methanol synthesis unit 205 yields a methanol-containing stream 207, which optionally comprises light ends, methanol, water, and fusel oil. Optionally, prior to the separation of the components contained in methanol-containing stream 207, the methanol-containing stream 207 is treated with a caustic medium, not shown, in a caustic wash unit, not shown, under conditions effective to increase the pH of the methanol-containing stream 207.

Meanwhile, second derivative syngas stream 203, or a portion thereof, is directed to fuel alcohol synthesis unit 206, wherein the syngas in the second derivative syngas stream 203 contacts a fuel alcohol synthesis catalyst composition under conditions effective to form fuel alcohol, e.g., C2-C4 alcohols, which is yielded from the fuel alcohol synthesis unit 206 in fuel alcohol-containing stream 208. Additionally, fuel alcohol-containing stream 208 optionally comprises methanol, light ends, water, and fusel oil. As with methanol-containing stream 207, fuel alcohol-containing stream 208 optionally is treated in a caustic wash unit, not shown, to increase the pH thereof. As shown in FIG. 2, the methanol-containing stream 207 is combined with the fuel alcohol-containing stream 208 to form combined alcohol-containing stream 209.

Combined alcohol-containing stream 209 preferably is directed to a separation zone, which comprises a light ends separation unit 210, such as a topping column, and a refining column 213. In the light ends separation unit 210, conditions are effective to separate the combined alcohol-containing stream 209 into light ends stream 211 and bottoms alcohol stream 212.

At least a portion of light ends stream 211 preferably is recycled to one or more of the syngas generation unit 201, the methanol synthesis unit 205, and/or the fuel alcohol synthesis unit 206. As shown, stream 224, the flow of which is regulated by flow control device 233, carries light ends from light ends stream 211 to one or more of these units. Specifically, stream 227 carries the light ends from stream 224 to the syngas generation unit 201. Similarly, stream 225 carries light ends from stream 224 to the fuel alcohol synthesis unit 206. Likewise, stream 226 carries light ends from stream 224 to the methanol synthesis unit 205. The flow of the light ends through these various streams optionally is controlled via flow control devices 229, 232 and 231. As shown, a portion of the components in stream 224 can be removed from the system via purge stream 228. The flow rate at which components are removed from the system via purge stream 228 optionally is controlled via flow control device 230.

In one embodiment, the light ends separation unit 210 also functions as a caustic wash unit. As shown, a caustic stream 235 is introduced to the light ends separation unit 210 under conditions effective to increase the pH of the combined alcohol-containing stream 209 after it has been introduced therein. Thus, bottoms alcohol stream 212 may include caustic salts from caustic stream 235.

As shown, bottoms alcohol stream 212 is directed to refining column 213, wherein water and optionally fusel oil, not shown, are separated from the methanol and fuel alcohol contained in bottoms alcohol stream 212. Thus, bottoms alcohol stream 212 is separated into a water-containing stream 215, a fusel oil stream, not shown, and a refined alcohol stream 214. Water-containing stream 215 preferably contains a weight majority of the caustic salts that were contained in bottoms alcohol stream 212.

Refined alcohol stream 214, which comprises largely methanol and fuel alcohol, is then directed to an OTO reactor 222 wherein the methanol and fuel alcohol contained in the refined alcohol stream 214 contact one or more molecular sieve catalyst compositions under conditions effective to form ethylene and propylene, which are yielded from the OTO reactor 222 in light olefins containing stream 223.

FIG. 3 illustrates another embodiment of the present invention wherein the methanol synthesis unit and the fuel alcohol synthesis unit are situated in series rather than in parallel. As shown, natural gas stream 300 comprising natural gas is directed to a syngas generation unit 301 wherein the natural gas is converted to syngas in syngas stream 302. Syngas generation unit 301 optionally comprises a steam reforming unit, a partial oxidation unit, an autothermal reforming unit, and/or a combined reforming unit, e.g., a unit that combines two or more of these reforming processes. As above, natural gas stream 300 optionally is saturated with water prior to or upon introduction into syngas generation unit 301. Syngas stream 302 preferably is directed to a compression zone, not shown, wherein the syngas stream 302 is compressed to a pressure favorable for conversion thereof to methanol. After compression, syngas stream 302 is directed to methanol synthesis unit 305 for conversion thereof to methanol. In the methanol synthesis unit, the syngas stream 302 contacts one or more methanol synthesis catalysts under conditions effective to convert at least a portion of the syngas to crude methanol, which is yielded from the methanol synthesis unit via methanol-containing stream 307. Optionally, unreacted syngas from methanol synthesis unit 305 is recycled to the compression zone.

Methanol-containing stream 307, which is yielded from the methanol synthesis unit 305, preferably comprises light ends, methanol, water and fusel oil. As shown, at least a portion of methanol-containing stream 307 is directed to a fuel alcohol synthesis unit 306, which preferably comprises a fuel alcohol synthesis zone. In the fuel alcohol synthesis unit 306, at least a portion of the methanol-containing stream 307 contacts carbon monoxide, preferably hydrogen, and optionally carbon dioxide in the presence of one or more fuel alcohol synthesis catalysts under conditions effective to form fuel alcohol. The fuel alcohol formed in fuel alcohol synthesis unit 306 is yielded therefrom via fuel alcohol-containing stream 308.

Depending on reaction conditions and the specific catalyst used in the fuel alcohol synthesis unit 306, all or a portion of the methanol that was introduced into the fuel alcohol synthesis unit 306 may be converted to fuel alcohol. As it is desirable according to the present invention to provide an alcohol-containing stream that comprises both methanol and fuel alcohol, a portion of the methanol from methanol-containing stream 307 optionally bypasses the fuel alcohol synthesis unit 306, as shown by bypass stream 337, the flow of which is controlled by flow control device 336. Ideally, as shown in FIG. 3, bypass stream 337 is recombined with fuel alcohol-containing stream 308 prior to the introduction thereof into the separation zone for removal of undesirable components therefrom.

As shown, fuel alcohol-containing stream 308, which comprises methanol, fuel alcohol, water, light ends, and fusel oil is introduced into light ends separation unit 310. In light ends separation unit 310, the light ends in fuel alcohol-containing stream 308 are separated from the other components contained therein. Specifically, in light ends separation unit 310, the fuel alcohol-containing stream 308 is subjected to conditions effective to form light ends stream 311 and bottoms alcohol stream 312. Light ends stream 311 preferably comprises a weight majority of the light ends that were contained in ethanol-containing stream 308, while the bottoms alcohol stream 312 comprises a weight majority of the methanol, fuel alcohol, water and fusel oil present in the fuel alcohol-containing stream 308.

Preferably, a portion of light ends stream 311 is directed through stream 324 to one or more of the syngas generation unit 301, the methanol synthesis unit 305, and/or the fuel alcohol synthesis unit 306. As illustrated, stream 324 is directed to the syngas generation unit 301 via stream 327, to the methanol synthesis unit 305 via stream 326, and to the fuel alcohol synthesis unit 306 via stream 325. The flow rate at which the light ends stream 311, or a portion thereof, is directed to these units may be varied by flow control devices 329, 331, 332, and/or 333. Preferably, a portion of the light ends are purged from the system via purge stream 328, the flow of which may be controlled by flow control device 330.

As indicated above, light ends separation unit 310 optionally also functions as a caustic wash unit. As shown, caustic stream 335 is introduced into light ends separation unit 310 under conditions effective to increase the pH of the bottoms alcohol stream 312. As a result, bottoms alcohol stream 312 optionally comprises caustic salts in addition to methanol, fuel alcohol, water and fusel oil. As shown, bottoms alcohol stream 312 is directed to a refining column 313 for removal of the water contained therein. Thus, refining column 313 operates to separate the bottoms alcohol stream 312 into a refined alcohol stream 314 and a water-containing stream 315. Preferably, water-containing stream 315 comprises a weight majority of the water that was present in the bottoms alcohol stream 312. Similarly, refined alcohol stream 314 preferably comprises a weight majority of the methanol and fuel alcohol contained in bottoms alcohol stream 312. Refining column 313 optionally also forms a side draw stream, not shown, whereby a weight majority of the fusel oil that was contained in bottoms alcohol stream 312 is removed therefrom. Refined alcohol stream 314, which comprises methanol, ethanol, and optionally C3-C4 or higher alcohols, may then be directed to an OTO reactor 322, wherein the methanol and ethanol (as well as the optional C3-C4 or higher alcohols) contained therein are converted to light olefins, which are yielded from the OTO reactor 322 via light olefins containing stream 323.

F. Controlling the Ration of Ethylene to Propylene Formed in an OTO Reaction System It has been discovered that ethanol has a selectivity for ethylene under OTO and ETO reaction conditions, which approaches 100 weight percent. Methanol, in contrast, produces ethylene and propylene in generally equal amounts under OTO and ETO reaction conditions. By increasing the amount of ethanol, e.g., from the fuel alcohol-containing stream, contained in an OTO feedstock, the amount of ethylene produced in the OTO reaction system relative to propylene can be advantageously increased.

In one aspect of the invention, the ratio of ethylene to propylene formed in an OTO reaction system can be controlled by varying the ratio of the methanol to ethanol that is sent to the OTO reaction system. As indicated above, methanol converts to ethylene and propylene in relatively equal amounts in an OTO reaction system, while ethanol converts almost entirely to ethylene. As a result, as the amount of ethanol contained in an OTO feedstock is increased relative to methanol, the amount of ethylene produced in the OTO reaction system will increase. Thus, the amount of ethylene relative to propylene formed in an OTO reaction system advantageously can be controlled by controlling the ratio of methanol to ethanol contained in the OTO feedstock.

The weight ratio of methanol to ethanol contained in an OTO feedstock can be controlled by a variety of ways. For example, if the integrated system comprises a methanol synthesis unit that is separate from the fuel alcohol synthesis unit, then one or more flow control devices may be used to control the flow of methanol from the methanol synthesis unit and the amount of fuel alcohol (and hence the amount of ethanol) from the fuel alcohol synthesis unit that is directed to the OTO reaction system. Additionally or alternatively, the amount and/or type of catalyst in the fuel alcohol synthesis unit and/or the methanol synthesis unit can be varied to control ratio of the alcohols formed therein. If the integrated system includes a single combined synthesis unit, which forms both the methanol and fuel alcohol, then the weight ratio of the methanol synthesis catalyst to the fuel alcohol synthesis catalyst contained in the combined synthesis unit can be controlled to provide a desired methanol to fuel alcohol weight ratio.

Additionally or alternatively, the reaction conditions in the fuel alcohol synthesis unit, e.g., temperature, can be varied to control ratio of the ethanol or C3+ alcohols formed therein. Generally, an increase in reaction temperature in a fuel alcohol synthesis unit, within reason, increases the amount of ethanol and other byproducts formed in the fuel alcohol synthesis unit.

Thus, in one aspect of the invention, the ratio of ethylene to propylene formed in an OTO reaction system can be controlled by varying the reaction temperature in an fuel alcohol synthesis unit, which, in cooperation with a methanol synthesis unit, produces the feedstock for the OTO reaction system. That is, an increase in the reaction temperature of a fuel alcohol synthesis unit will increase the amount of ethanol formed, which, ultimately, will increase the amount of ethylene that is formed in the OTO reaction system. In this manner, the amount of ethylene relative to propylene formed in an OTO reaction system advantageously can be controlled by controlling the reaction temperature of the ethanol synthesis unit.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for producing light olefins, the process comprising the steps of:
    (a) contacting a first syngas stream comprising carbon monoxide, carbon dioxide and hydrogen with a methanol synthesis catalyst under first conditions effective to form a methanol-containing stream comprising methanol and water;
    (b) contacting a second syngas stream comprising carbon monoxide, carbon dioxide and hydrogen with a fuel alcohol synthesis catalyst under second conditions effective to form a fuel alcohol-containing stream comprising ethanol, propanol and butanol;
    (c) combining at least a portion of the methanol-containing stream with at least a portion of the fuel alcohol-containing stream to form a combined stream having a methanol to $C_2$-$C_4$ alcohol weight ratio of from about 0.1 to about 4.0 and having a butanol content of less than 3 weight percent; and
    (d) contacting at least a portion of the combined stream with a molecular sieve catalyst composition in a reaction zone under third conditions effective to form ethylene and propylene.

2. The process of claim 1, wherein the molecular sieve catalyst composition comprises a molecular sieve selected from the group consisting of: MeAPSO, SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

3. The process of claim 1, wherein the molecular sieve catalyst composition comprises a zeolitic molecular sieve catalyst composition.

4. The process of claim 1, wherein the methanol to $C_2$-$C_4$ alcohol weight ratio is from about 0.33 to about 3.0.

5. The process of claim 1, wherein the fuel alcohol synthesis catalyst comprises a microporous zeolitic material.

6. The process of claim 1, wherein the fuel alcohol synthesis catalyst comprises one or more of $Cu/ZnO/Cr_2O_3$ and $Cu/ZnO/Al_2O_3$, and wherein the fuel alcohol synthesis catalyst optionally is alkali promoted.

7. The process of claim 1, wherein the fuel alcohol synthesis catalyst comprises an oxide of one or more of zinc, chromium, copper, cobalt, and nickel, and wherein the fuel alcohol synthesis catalyst optionally is alkali, lanthanum or cerium promoted.

8. The process of claim 1, wherein the fuel alcohol synthesis catalyst comprises one or more of $MoS_2$ and $Co/MoS_2$, and wherein the fuel alcohol synthesis catalyst optionally is alkali promoted.

9. The process of claim 1, wherein the methanol synthesis catalyst comprises an oxide of one or more of copper, zinc and aluminum.

10. The process of claim 1, wherein the process further comprises the step of:
    (e) removing water from the combined stream prior to step (d).

11. The process of claim 1, wherein the process further comprises the steps of:
    (e) contacting a natural gas stream with oxygen under fourth conditions effective to convert the natural gas stream into an initial syngas stream; and
    (f) separating the initial syngas stream into the first syngas stream and the second syngas stream.

12. The process of claim 1, wherein the ethylene and propylene are yielded in an effluent stream having an ethylene to propylene weight ratio of greater than 1.0.

13. The process of claim 12, wherein the ethylene to propylene weight ratio is from about 1.1 to about 2.5.

14. The process of claim 13, wherein the ethylene to propylene weight ratio is from about 1.2 to about 2.0.

15. The process of claim 1, wherein steps (a) and (b) occur in parallel.

16. The process of claim 1, wherein the fuel alcohol-containing stream comprises less than about 75 weight percent methanol, based on the total weight of the fuel alcohol-containing stream.

17. The process of claim 16, wherein the fuel alcohol-containing stream comprises less than about 65 weight percent methanol, based on the total weight of the fuel alcohol-containing stream.

18. The process of claim 17, wherein the fuel alcohol-containing stream comprises less than about 60 weight percent methanol, based on the total weight of the fuel alcohol-containing stream.

19. The process of claim 1, wherein the fuel alcohol-containing stream comprises at least about 10 weight percent ethanol, based on the total weight of the fuel alcohol-containing stream.

20. The process of claim 19, wherein the fuel alcohol-containing stream comprises at least about 25 weight percent ethanol, based on the total weight of the fuel alcohol-containing stream.

21. The process of claim 1, wherein the fuel alcohol-containing stream comprises at least about 10 weight percent $C_3$-$C_4$ alcohols, based on the total weight of the fuel alcohol-containing stream.

22. The process of claim 1, wherein the process further comprises the steps of:
(e) separating a majority of the ethylene from a majority of the propylene to form an ethylene-containing stream and a propylene-containing stream; and
(f) contacting the ethylene-containing stream with a polymerization catalyst under fourth conditions effective to convert at least a portion of the ethylene contained therein to polyethylene.

23. The process of claim 1, wherein the process further comprises the steps of:
(e) separating a majority of the ethylene from a majority of the propylene to form an ethylene-containing stream and a propylene-containing stream; and
(f) contacting the propylene-containing stream with a polymerization catalyst under fourth conditions effective to convert at least a portion of the propylene contained therein to polypropylene.

24. A process for producing light olefins, wherein the process comprises the steps of:
(a) contacting a first syngas stream comprising carbon monoxide, carbon dioxide and hydrogen with a methanol synthesis catalyst under first conditions effective to form a methanol-containing stream comprising methanol and water;
(b) contacting a second syngas stream comprising carbon monoxide, carbon dioxide and hydrogen with a fuel alcohol synthesis catalyst under second conditions effective to form a fuel alcohol-containing stream comprising ethanol, propanol and butanol;
(c) combining at least a portion of the methanol-containing stream with at least a portion of the fuel alcohol-containing stream to form a combined stream having a methanol to $C_2$-$C_4$ alcohol weight ratio of from about 0.1 to about 4.0 and having a butanol content of less than 3 weight percent;
(d) contacting at least a portion of the combined stream with a molecular sieve catalyst composition in a reaction system under third conditions effective to convert the methanol, the ethanol, optionally the propanol and optionally the butanol to light olefins;
(e) yielding an effluent stream from the reaction system, wherein the effluent stream comprises ethylene and propylene and has an ethylene to propylene weight ratio of from about 0.9 to about 3.0.

25. The process of claim 24, wherein the ethylene to propylene weight ratio is from about 1.1 to about 2.5.

26. The process of claim 25, wherein the ethylene to propylene weight ratio is from about 1.2 to about 2.0.

27. The process of claim 24, wherein the molecular sieve catalyst composition comprises a molecular sieve selected from the group consisting of: MeAPSO, SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

28. The process of claim 24, wherein the molecular sieve catalyst composition comprises a zeolitic molecular sieve catalyst composition.

29. The process of claim 24, wherein the methanol to $C_2$-$C_4$ alcohol weight ratio is from about 0.33 to about 3.0.

30. The process of claim 24, wherein the process further, comprises the steps of:
(f) removing the water from the combined stream before step (d).

31. The process of claim 24, wherein the fuel alcohol synthesis catalyst comprises a microporous zeolitic material.

32. The process of claim 24, wherein the fuel alcohol synthesis catalyst comprises one or more of $Cu/ZnO/Cr_2O_3$ and $Cu/ZnO/Al_2O_3$, and wherein the fuel alcohol synthesis catalyst optionally is alkali promoted.

33. The process of claim 24, wherein the fuel alcohol synthesis catalyst comprises an oxide of one or more of zinc, chromium, copper, cobalt, and nickel, and wherein the fuel alcohol synthesis catalyst optionally is alkali, lanthanum or cerium promoted.

34. The process of claim 24, wherein the fuel alcohol synthesis catalyst comprises one or more of $MoS_2$ and $Co/MoS_2$, and wherein the fuel alcohol synthesis catalyst optionally is alkali promoted.

35. The process of claim 24, wherein the methanol synthesis catalyst comprises an oxide of one or more of copper, zinc and aluminum.

36. The process of claim 24, wherein the process further comprises the steps of:
(f) contacting a natural gas stream with oxygen under fourth conditions effective to convert the natural gas stream into an initial syngas stream; and
(g) separating the initial syngas stream into the first syngas stream and the second syngas stream.

37. The process of claim 24, wherein steps (a) and (b) occur in parallel.

38. The process of claim 24, wherein the fuel alcohol-containing stream comprises less than about 75 weight percent methanol, based on the total weight of the fuel alcohol-containing stream.

39. The process of claim 38, wherein the fuel alcohol-containing stream comprises less than about 65 weight percent methanol, based on the total weight of the fuel alcohol-containing stream.

40. The process of claim 39, wherein the fuel alcohol-containing stream comprises less than about 60 weight percent methanol, based on the total weight of the fuel alcohol-containing stream.

41. The process of claim 24, wherein the fuel alcohol-containing stream comprises at least about 10 weight percent ethanol, based on the total weight of the fuel alcohol-containing stream.

42. The process of claim 41, wherein the fuel alcohol-containing stream comprises at least about 25 weight percent ethanol, based on the total weight of the fuel alcohol-containing stream.

43. The process of claim 24, wherein the fuel alcohol-containing stream comprises at least about 10 weight percent $C_3$-$C_4$ alcohols, based on the total weight of the fuel alcohol-containing stream.

44. The process of claim 24, wherein the process further comprises the steps of:
(f) separating a majority of the ethylene from a majority of the propylene to form an ethylene-containing stream and a propylene-containing stream; and (g) contacting the ethylene-containing stream with a polymerization catalyst under fourth conditions effective to convert at least a portion of the ethylene contained therein to polyethylene.

45. The process of claim 24, wherein the process further comprises the steps of:

(f) separating a majority of the ethylene from a majority of the propylene to form an ethylene-containing stream and a propylene-containing stream; and (g) contacting the propylene-containing stream with a polymerization catalyst under fourth conditions effective to convert at least a portion of the propylene contained therein to polypropylene.

46. The process of claim 1, wherein the propanol content of the combined stream is less than 5 weight percent.

47. The process of claim 24, wherein the propanol content of the combined stream is less than 5 weight percent.

* * * * *